US008916606B2

(12) United States Patent
Tour et al.

(10) Patent No.: US 8,916,606 B2
(45) Date of Patent: Dec. 23, 2014

(54) THERAPEUTIC COMPOSITIONS AND METHODS FOR TARGETED DELIVERY OF ACTIVE AGENTS

(75) Inventors: James M. Tour, Bellaire, TX (US); Jacob Berlin, Monrovia, CA (US); Tam Pham, Renton, WA (US); Jeffrey N. Myers, Bellaire, TX (US); Daisuke Sano, Yokohama (JP)

(73) Assignees: William Marsh Rice University, Houston, TX (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/504,716

(22) PCT Filed: Oct. 27, 2010

(86) PCT No.: PCT/US2010/054321
§ 371 (c)(1), (2), (4) Date: Jul. 3, 2012

(87) PCT Pub. No.: WO2011/087548
PCT Pub. Date: Jul. 21, 2011

(65) Prior Publication Data
US 2012/0302816 A1 Nov. 29, 2012

Related U.S. Application Data

(60) Provisional application No. 61/255,309, filed on Oct. 27, 2009.

(51) Int. Cl.
*A61K 31/335* (2006.01)
*A61K 47/00* (2006.01)
(Continued)

(52) U.S. Cl.
CPC .............. *C07K 16/2854* (2013.01); *B82Y 5/00* (2013.01); *A61K 51/1268* (2013.01); *A61K*
(Continued)

(58) Field of Classification Search
CPC .......... B82Y 30/00; B82Y 40/00; B82Y 5/00; A61K 47/48884; A61K 47/48869; A61K 47/48961; A61K 31/337; A61K 47/48238; A61K 47/48369; A61K 9/0092; A61K 47/48215; A61K 31/165; A61K 31/704; A61K 38/16; A61K 38/1808; A61K 39/395; A61K 47/48146; A61K 47/48953; A61K 51/1268; A61K 9/0019; A61K 9/51; A61K 9/5115; A61N 1/00; A61N 1/205; A61N 1/325; A61N 1/327; A61N 1/362; A61N 1/37205
See application file for complete search history.

(56) References Cited

U.S. PATENT DOCUMENTS 5,004,606 A 4/1991 Frincke et al.
2004/0076681 A1* 4/2004 Dennis et al. ................. 424/489
(Continued)

FOREIGN PATENT DOCUMENTS

WO WO 2008118960 A2 * 10/2008

OTHER PUBLICATIONS

Drug Bank, "Paclitaxel", Open Data Drug & Drug Target Database, <http://www.drugbank.ca/drugs/DB01229>, Created Jun. 13, 2005, Updated May 19, 2013, p. 1-11.*
(Continued)

*Primary Examiner* — Tracy Vivlemore
*Assistant Examiner* — Monica Shin
(74) *Attorney, Agent, or Firm* — Winstead PC

(57) ABSTRACT

The present invention pertains to therapeutic compositions that comprise: (1) a nanovector, (2) an active agent; and (3) a targeting agent, wherein the active agent and the targeting agent are non-covalently associated with the nanovector. The present invention also pertains to methods of treating various conditions in a subject by utilizing the above-described therapeutic compositions. Methods of making the therapeutic compositions are also a subject matter the present invention.

13 Claims, 31 Drawing Sheets

(51) Int. Cl.
- *A61K 38/00* (2006.01)
- *A61K 9/00* (2006.01)
- *B82Y 5/00* (2011.01)
- *A61K 51/12* (2006.01)
- *A61K 47/48* (2006.01)
- *C07K 16/28* (2006.01)

(52) U.S. Cl.
CPC .............. 47/48884 (2013.01); *A61K 47/48961* (2013.01); *Y10S 977/75* (2013.01); *Y10S 977/746* (2013.01); *Y10S 977/906* (2013.01); *Y10S 977/842* (2013.01)
USPC .......... 514/449; 514/44 R; 514/773; 514/1.1; 424/400; 977/750; 977/746; 977/906; 977/842

(56) References Cited

U.S. PATENT DOCUMENTS

| | | | | |
|---|---|---|---|---|
| 2005/0100960 | A1* | 5/2005 | Dai et al. | 435/7.1 |
| 2008/0175892 | A1* | 7/2008 | Wilson et al. | 424/450 |
| 2008/0193490 | A1 | 8/2008 | Hirsch et al. | |
| 2009/0087493 | A1* | 4/2009 | Dai et al. | 424/490 |
| 2009/0214101 | A1 | 8/2009 | Wilson et al. | |

OTHER PUBLICATIONS

International Search Report and Written Opinion for PCT/US2010/054321. Aug. 17, 2011.
International Preliminary Report on Patentability for PCT/US2010/054321. May 10, 2012.
Strebhart et al., Paul Ehrlich's magic bullet concept: 100 years of progress, Nature Rev. 2008, 8, 473-480.
Safavy et al., Synthesis and Biological Evaluation of Paclitaxel-C225 Conjugate as a Model for Targeted Drug Delivery, Bioconjugate Chem 2003, 14, 302-310.
Wolinsky et al., Therapeutic and diagnostic applications of dendrimers for cancer treatment, Adv. Drug Deliv. Rev. 2008, 60, 1037-1055.
Lukyanov et al., Tumor-targeted liposomes: doxorubicin-loaded long-circulating liposomes modified with anti-cancer antibody, J. Contr. Rel. 2004, 100, 135-144.
Weng et al., Carbon nanotubes as a protein toxin transporter for selective HER2-positive breast cancer cell destructionw, Mol. Bio Syst., 2009, 5, 1224-1231.
Chen et al., Soluble Ultra-Short Single-Walled Carbon Nanotubes, J. Am. Chem. Soc. 2006, 128, 10568-10571.
Stephenson, et al., Repetitive Functionalization of Water-Soluble Single-Walled Carbon Nanotubes. Addition of Acid-Sensitive Addends, Chem. Mater. 2007, 19, 3491-3498.
Berlin et al., Effective Drug Delivery, In Vitro and In Vivo, by Carbon-Based Nanovectors Noncovalently Loaded with Unmodified Paclitaxel, ACS Nano 2010, 4, 4621-4636.
Lucente-Schultz et al., Antioxidant Single-Walled Carbon Nanotubes, J. Am. Chem. Soc. 2009, 131, 3934-3941.
Price et al., Aggressively Oxidized Ultra-Short Single-Walled Carbon Nanotubes Having Oxidized Sidewalls, Chem. Mater. 2009, 21, 3917-3923.
Myers et al., An Orthotopic Nude Mouse Model of Oral Tongue Squamous Cell Carcinoma, Clin. Cancer Res. 2002, 8, 293-298.
Dijk et al. Synthesis and Applications of Biomedical and Pharmaceutical Polymers via Click Chemistry Methodologies, Bioconjugate Chem. 2009, 20, 2001-2016.
Hong et al., Feasibility of metal recovery from soil using DTPA and its biostability, J. Hazard. Mater. 2002, 94, 253-272.
Montalbetti et al., Amide bond formation and peptide coupling, Tetrahedron 2005, 61, 10827-10852.
Theodossis et al., Firefly Luciferin-activated Rose Bengal: In Vitro Photodynamic Therapy by Intracellular Chemiluminescence in Transgenic NIH 3T3 Cells, Cancer Research 2005, 63, 1818-1821.
Higginbotham et al., Lower-Defect Graphene Oxide Nanoribbons from Multiwalled Carbon Nanotubes, ACS Nano 2010, 4, 2059-2069.
Kosynkin et al., Longitudinal unzipping of carbon nanotubes to form graphene nanoribbons, Nature 2009, 458, 872-826.
Riehemann et al., Nanomedicine—Challenge and Perspectives, Ang. Chem. Int. Ed. 48, 872-897 (2009).
Hirsch et al., Nanoshell-mediated near-infrared thermal therapy of tumors under magnetic resonance guidance, Proc. Natl. Acad. Sci. USA 100, 13549-54 (2003).
Wrle-Knirsch et al., Oops They Did It Again! Carbon Nanotubes Hoax Scientists in Viability Assays, Nano Lett. 2006, 6, 1261-1268.

* cited by examiner

A

B

C

G

H

I

PTX/PEG-HCC　　　　　Cet/PTX/PEG-HCC

A

B

C

D

1) Control (Saline only)
2) 10 μL Cetuximab (0.0359 mg/ml)
3) 10 μL Cetuximab/PEGHCC (0.0359 mg/ml + 100mg/ml)
4) 10 μL PEGHCC (100 mg/ml)
PC) 2 μg Cetuximab

A

B

THERAPEUTIC COMPOSITIONS AND METHODS FOR TARGETED DELIVERY OF ACTIVE AGENTS

CROSS REFERENCE TO RELATED APPLICATIONS

This application claims priority to United States Provisional Patent Application No. 61/255,309, the entirety of which is incorporated herein by reference.

STATEMENT REGARDING FEDERALLY SPONSORED RESEARCH

This invention was made with government support under grant no. W81XWH-08-2-0143 awarded by the United States Army through the Traumatic Brain Injury Consortium; grant no. EEC-0647452 awarded by the National Science Foundation (NSF) through the NSF Nanoscale Science and Engineering Initiative and the NSF Center for Biological and Environmental Nanotechnology; and grant no. W8XWH-07-2-0101 awarded by the Department of Defense through the Alliance for NanoHealth. The government has certain rights in the invention.

BACKGROUND OF THE INVENTION

Successful treatment of many diseases that have caused significant worldwide public health problems have been limited in part by the toxicity and lack of specificity of systemic treatments (e.g., cancer, microbial infections, traumatic brain injury, etc.). Thus, research in targeted drug delivery strives for a significant in vivo increase in the therapeutic index of various treatments (i.e., specific toxicity of a drug at a desired site without significant effects, on other sites in the body).

With respect to cancer treatment, one method is to transport the drug with a monoclonal antibody that binds to a receptor that is over-expressed on tumor cells. Such methods directly attach the drug to the antibody. Such methods also attach both the drug and antibody to a platform. However, a major hurdle with such targeted drug delivery methods is the long synthetic route to, make these complex compounds. Furthermore, the efficacy of such methods usually requires. improvement. Therefore, more efficient and effective approaches to targeted drug delivery are desired for treating various diseases and conditions (including cancer).

BRIEF SUMMARY OF THE INVENTION

In some embodiments, the present disclosure pertains to therapeutic compositions that comprise: (1) a nanovector; (2) an active agent; and (3) a targeting agent. In such the active agent and the targeting agent are non-covalently associated with the nanovector. In more specific embodiments, the nanovector comprises a polyethylene glycol-functionalized hydrophilic carbon cluster (PEG-HCC). In some embodiments, the active agent comprises an anti-cancer drug (e.g., Paclitaxel). In additional embodiments, the targeting agent comprises a monoclonal antibody that targets an over-expressed receptor on cancer cells (e.g., Cetuximab, an epidermal growth factor receptor inhibitor). In additional embodiments, the active agent and the nanovector are the same molecule (e.g., PEG-HCC)

Additional embodiments of the present disclosure pertain to methods of treating a condition in a subject by administering a therapeutic composition of the present disclosure to the subject. Conditions to be treated can include, without limitation: cancer, microbial infections, and oxidative stress (e.g., oxidative stress caused by traumatic brain injury). In further embodiments, such treatment methods also comprise the administration of radiation to the subject before, during or after administering the therapeutic composition.

Other embodiments of the present disclosure pertain to methods of making therapeutic compositions of the present disclosure. Such methods generally comprise the non-covalent association of a nanovector and a targeting agent with an active agent. In some embodiments, such associations may occur by sequestration.

The methods and compositions of the present invention allow for more cost-effective and efficient approaches for treating many diseases with reduced side effects, streamlined treatment formulations, and improved patient outcomes.

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated in the appended Figures. Understanding that these Figures depict only typical embodiments of the invention and are therefore not to be considered limiting of its scope, the invention will be described with additional specificity and detail through the use of the accompanying Figures in which:

FIG. 1 illustrates the characterization of hydrophilic carbon clusters (HCCs) and PEG-functionalized HCCs (PEG-HCCs).

FIG. 2A depicts the addition of PTX to PEG-HCCs (the addition was done slowly in methanol to an aqueous solution of the PEG-HCCs, followed by evaporation of the methanol).

FIG. 2B depicts the sequestered PTX in the PEG-HCC matrix.

FIG. 2C shows images of the following PBS solutions approximately five minutes after mixing (in order from left to right): HCCs in PBS (insoluble); PEG-HCCs in PBS (soluble); PTX/PEG-HCCs, where PTX is overloaded; and PTX/PEG-HCCs, where PTX is predominantly sequestered and thereby in solution.

FIG. 4A shows the change in tumor volume of the mice after treatment. The three arrows along the x-axis denote the three days of injection of treatment. Tumor volume was measured twice weekly. Error bars are standard errors. A paired t-test was used to compare the differences in tumor volume.

FIG. 4B shows animal survival over 50 days, as analyzed by the Kaplan-Mieir method and compared with log-rank tests.

FIG. 8A depicts the preparation of Cet/PTX/PEG-HCCs by non-covalently 'wrapping' PTX/PEG-HCCs with Cetuximab.

FIG. 8B shows the design of a targeting experiment to test the ability of Cet/PTX/PEG-HCC to selectively deliver Paclitaxel in vitro.

FIG. 8C illustrates the in vitro targeting efficacy for Cet/PTX/PEG-HCCs.

FIG. 8D shows the inhibition of epidermal growth factor receptor (EGFR) targeting by exogenous EGF.

FIG. 12A shows results from immunoprecipitation of EGFR with Cetuximab Cet/PEG-HCC and PEG-HCC.

FIG. 12B shows results from the same immunoprecipitation studies run with lower concentrations of the reagents and a shorter development time to better illustrate the difference between the free Cetuximab and the Cet/PEG-HCCs.

FIG. 13 is a demonstration of the in vivo targeting of Cet-directed PTX/PEG-HCCs. Mice with orthotopically established oral tongue tumors (OSC-19) were injected once weekly (at days 12, 19 and 26) with various treatments (saline, Cetuximab, Cet/PEG-HCCs, PTX/Cremophor, Cet/PTX/Cremophor, and Cet/PTX/PEG-HCCs).

FIG. 14 is a demonstration of the in vivo targeting of Cet-directed PTX/PEG-HCCs. Mice with orthotopically established oral tongue tumors (Fadu) were injected once weekly (at days 12, 19 and 26) with various treatment regimens (saline, Cetuximab, Cet/PEG-HCCs, PTX/Cremophor, Cet/PTX/Cremophor, and Cet/PTX/PEG-HCCs).

FIG. 15A shows the design of the joint flank model used in the treatment.

FIG. 15B shows the ratio of the two tumor volumes during treatment with control (black diamonds), PTX/PEG-HCCs (closed circles) and Cet/PTX/PEG-HCCs (open circles). The arrows denote the days of injection.

FIG. 15C shows the change in tumor volume of OSC-19 during treatment. The arrows denote the days of injection.

FIG. 15D shows the change in tumor volume of MCF-7 during treatment. Black arrows indicate the two treatments.

FIG. 15E shows images of a mouse from each treatment group at day 20.

FIG. 17 shows the survival of OSC-19 cells in a co-culture with MCF-7 cells when treated with PTX/PEG-HCCs, PTX/PEG-GONRs (PEGylated graphite oxide nanoribbons with PTX), and PTX/PEG-OCBs (PEGylated oxidized carbon black with PTX).

DETAILED DESCRIPTION OF EXEMPLARY EMBODIMENTS

Figure 1A:
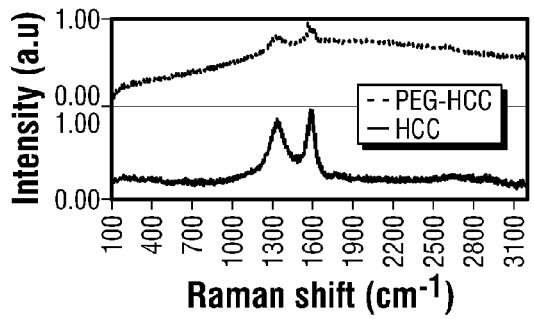
FIG. 1A shows Raman spectra of both compounds indicating that HCCs and PEG-HCCs are free of radial-breathing modes and have similar peak ratios (fluorescence of the PEG-HCCs causes the baseline rise for that spectrum).

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Antibodies and proteins can be used to target the delivery of drugs. However, several difficulties have presented themselves for the development of effective targeted therapies. Direct covalent-bond attachment of the drug to the antibody often requires a significant synthetic effort. Perhaps more significantly, it is challenging to attach a sufficient amount of the drug to each antibody without compromising the solubility or activity of the antibody or the drug.

An alternative strategy is to make use of a third body platform, such as a dendrimer, to increase the loading of drug relative to antibody. This approach entails a much more difficult synthetic effort as both the drug and antibody must be covalently attached to the platform. Thus, there remains a pressing need for a simple and effective targeted formulation of cytotoxic cancer drugs and other active agents.

To address these needs, there has been recent interest in developing targeted drug delivery formulations in which the components are non-covalently attached. This has included complexes of just the targeting protein and the drug, as well as constructs where the drug and protein are bound to a third body platform. There has even been recent attention given to using carbon nanomaterials for non-covalent binding of targeting antibodies. However, to the best of Applicants' knowledge, this disclosure describes the first example of a nanovector that alone is soluble in biological media, which can then be non-covalently loaded with a drug and targeting protein.

As set forth in more detail below, the ability of these loaded nanovectors to target the delivery of the drug has been demonstrated in vitro and in vivo.

Various embodiments of the present disclosure pertain to therapeutic compositions that comprise: (1) a nanovector; (2) an active agent; and (3) a targeting agent. In such embodiments, the active agent and the targeting agent are non-covalently associated with the nanovector. Some therapeutic compositions of the present disclosure may also comprise more than one type of nanovector, active agent, and/or targeting agent. Additional embodiments of the present disclosure pertain to methods of treating a condition in a subject by administering a therapeutic composition of the present disclosure to the subject.

Nanovectors

Nanovectors suitable for use in the present disclosure generally refer to particles that are capable of non-covalently associating with an active agent and a targeting agent. Nanovectors in the present disclosure also refer to particles that are capable of delivering an active agent to a targeted area. In some embodiments, the nanovectors of the present disclosure are soluble in water.

In some embodiments, nanovectors of the present disclosure are derived from at least one of single-walled nanotubes (SWNTs), oxidized SWNTs, multi-walled nanotubes (MWNTs), oxidized MWNTs, graphene, graphene nanoribbons, graphite, graphite oxide nanoribbons, carbon black, oxidized carbon black, and other nanoparticles. In some embodiments, the nanovectors may be functionalized by one or more molecules, polymers, chemical moities, and/or functional groups. In some embodiments, the above-described nanovectors can also serve as potent antioxidants (i.e., active agents) due to their conjugated carbon core frameworks.

In some embodiments, the nanovector is a hydrophilic carbon cluster (HCC). In some embodiments, HCCs generally refer to oxidized carbon nanotubes. Such nanotubes are generally referred to as ultra-short SWNTs (US-SWNTs). Therefore, for the purposes of the present disclosure, US-SWNTs are synonymous with HCCs.

In some embodiments, US-SWNTs (i.e., HCCs) may be produced by reacting SWNTs in sulfuric acid (or nitric acid) to produce a shortened carbon nanotube characterized by opening of the nanotube ends. This may be followed by the functionalization of the open ends with a plurality of carboxylic acid groups. In some embodiments, the HCC may be an oxidized graphene.

In more specific and preferred embodiments, the nanovector of the present disclosure is a polyethylene glycol-functionalized HCC (PEG-HCC). Various PEG-HCCs and methods of making them are disclosed in the following articles: Berlin et al., *ACS Nano* 2010, 4, 4621-4636; Lucente-Schultz et al., *J. Am. Chem. Soc.* 2009, 131, 3934-3941; Chen et al., *J. Am. Chem. Soc.* 2006, 128, 10568-10571; Stephenson, et al., *Chem. Mater.* 2007, 19, 3491-3498; Price et al., *Chem. Mater.* 2009, 21, 3917-3923. The entirety of the above-referenced articles are incorporated herein by reference.

Other suitable PEGylated carbon nanomaterials can also be used as nanovectors, as known by persons of ordinary skill in the art. Non-limiting examples include PEGylated graphite oxide nanoribbons (PEG-GONR) and PEGylated oxidized carbon black (PEG-OCB).

Additional suitable nanovectors, including PEG-HCCs, are disclosed in U.S. patent application Ser. No. 12/245,438, the entirety of which is incorporated herein by reference.

Other suitable nanovectors not disclosed here can also be envisioned by a person of ordinary skill in the art.

Active Agents

Active agents of the present disclosure generally refer to biologically active compounds, such as compounds that can be used to treat one or more conditions in a subject (e.g., human being). For instance, in various embodiments, active agents of the present disclosure may refer to anti-cancer drugs, antibiotics, chemotherapeutics, antioxidants, and anti-inflammatory drugs.

The active agents of the present disclosure may also be derived from various compounds. For instance, in various embodiments, the active agents of the present disclosure can be small molecules, proteins, aptamers, DNA, anti-sense oligo nucleotides, miRNA, siRNA, and the like. In more specific and preferred embodiments, the active agent is Paclitaxel (PTX, also known as Taxol® when contained in a commercial excipient, Cremaphor EL, which is a PEGylated castor oil with ethanol), a mitotic inhibitor used in cancer chemotherapy. In other suitable embodiments, the active agent is an antioxidant, such as butylated hydroxytoluene (BHT).

In other embodiments, the active agent and the nanovector are the same molecule. In a specific embodiment, the active agent and the targeting agent are PEG-HCC. As set forth in more detail below, PEG-HCC has anti-oxidant activity. Other suitable active agents not disclosed here can also be envisioned by a person of ordinary skill in the art.

Targeting Agents

Targeting agents of the present disclosure generally refer to compounds that target a particular cell, organ, and/or tissue for which treatment is desired. In various embodiments, the targeting agent may be compounds such as antibodies, RNA, DNA, aptamers, small molecules, dendrimers, and/or proteins. In more specific embodiments, the targeting agent can be a monoclonal or polyclonal antibody. In particular embodiments, the antibody may be a chimeric antibody or an antibody fragment (e.g., Fab fragment of a monoclonal antibody).

In further embodiments, the targeting agent may be an antibody that specifically targets epidermal growth factor receptors (e.g., Cetuximab). As set forth in more detail below, epidermal growth factor receptors (EGFRs) are over-expressed in many types of cancer cell lines. Thus, anti-EGFR antibodies and other EGFR inhibitors may be used to deliver anti-cancer agents to cancer cell lines in some embodiments.

In other embodiments, the targeting agent can be an anti-body that recognizes one or more markers on oxidatively damaged cells and/or tissues. For instance, in some embodiments, the targeting agent may be an anti-body that recognizes a protein that is unregulated on endothelial cells in response to inflammation or injury. In a more specific embodiment, the targeting agent is an antibody that recognizes p-selectin, a cell adhesion molecule that is upregulated on the surfaces of activated endothelial cells in response to inflammation.

In other embodiments, the targeting agent may facilitate transport of an antioxidant active agent across the blood brain barrier to treat traumatic brain injury (TBI). For instance, in a specific embodiment, the targeting agent is an anti-body that recognizes the transferrin receptor, a carrier protein for the import of iron into cells (including red blood cells). Other suitable active agents can also be envisioned by a person of ordinary skill in the art.

Administration of Therapeutic Compositions

Further embodiments of the present disclosure pertain to methods of treating a condition in a subject by administering one or more of the above-described therapeutic compositions to the subject.

Treated Conditions

The methods of the present disclosure can be used to treat various conditions. For instance, in some embodiments, the methods of the present disclosure may be used to treat various types of cancer (e.g., breast cancer, head and neck cancer, colorectal cancer, lymphatic cancer, etc.). In such embodiments, the active agent can be an anti-cancer drug (e.g., Paclitaxel). Likewise, the targeting agent may be a compound that recognizes one or more markers on a cancer cell. For instance, the targeting agent may be an antibody that recognizes the epidermal growth factor receptor, which is over-expressed in many cancer cell; lines. In more specific embodiments, the cancer-treating methods of the present disclosure may utilize a therapeutic composition where the nanovector is PEG-HCC, the active agent is Paclitaxel, and the targeting agent is Cetuximab.

In other embodiments, the methods of the present disclosure can be used to treat microbial infections, such as bacterial, viral, and/or fungal infections. In some of such embodiments, the active agent can be an antibiotic, and the targeting agent can be an antibody that recognizes one or more markers on the pathogenic microbes and/or infected cells.

In further embodiments, the methods of the present disclosure can be used to treat oxidative stress, such as oxidative stress caused by traumatic brain injury. In some of such embodiments, the active agent can be an antioxidant (e.g., butylated hydroxytoluene or BHT). In other embodiments, the nanovector core itself can be an antioxidant. In other embodiments, oxidative stress-treating methods of the present disclosure may utilize a therapeutic composition where the nanovector is PEG-HCC, the active agent is BHT, and the targeting agent is an anti-P selectin antibody.

Applicants further envision the use of the methods of the present disclosure to target specific central nervous system (CNS) compartments, such as the intravascular space, endothelial cells and possibly the brain parenchyma by altering bound proteins that determine this distribution. Such an achievement will not only allow the testing of important hypotheses, such as the contribution of vascular dysfunction to brain injury, but the possibility of a targeted treatments that ultimately will reduce the likelihood of toxicity while increasing the chances of benefit.

A person of ordinary skill in the art will recognize that the methods of the present disclosure can also be used to treat other conditions that have not been specifically described above. Furthermore, a person of ordinary skill in the art will recognize that various subjects may be treated with the methods and compositions of the present disclosure.

Subjects

In some embodiments, the methods and compositions of the present disclosure may be used to treat human beings. In some embodiments, the subjects being treated may be in need of such treatment for one or more conditions. In other embodiments, the subjects may be non-human animals, such as mice, rats, other rodents, or larger mammals, such as dogs, monkeys, pigs, cattle and horses.

Modes of Administration

The therapeutic compositions of the present disclosure can be administered to subjects by various methods known to persons of ordinary skill in the art. For instance, the therapeutic compositions of the present disclosure can be administered by oral administration, inhalation, subcutaneous administration (sub-q), intravenous administration (I.V.), intraperitoneal administration (I.P.), intramuscular administration (I.M.), and/or intrathecal injection. In further embodiments of the present disclosure, the therapeutic compositions of the present disclosure can be administered by topical application (e.g, transderm, ointments, creams, salves, eye drops, and the like). Additional modes of administration can also be envisioned by persons of ordinary skill in the art.

Formulation of Therapeutic Compositions

Additional embodiments of the present disclosure generally pertain to methods of making therapeutic compositions of the present disclosure. Such methods generally comprise: (1) non-covalently associating a nanovector with an active agent; and (2) non-covalently associating a targeting agent with the nanovector. In some embodiments, one or more of the above-mentioned associations occur by sequestration. In further embodiments, one or 'more of the associations occur by adsorption, ionic bonding, dipole-dipole interactions, hydrogen' bonding, and other non-covalent interactions known to persons of ordinary skill in the art.

Therapeutic compositions of the present disclosure can be formulated in conventional manners known to persons of ordinary skill in the art. In some embodiments, the formulation may also utilize one or more physiologically acceptable carriers or excipients. The pharmaceutical compositions can comprise formulation materials for modifying, maintaining, or preserving various conditions, including pH, osmolarity, viscosity, clarity, color, isotonicity, odor, sterility, stability, rate of dissolution or release, and/or adsorption or penetration of the composition. Suitable formulation materials include, but are not limited to: amino acids (e.g., glycine); antimicrobials; antioxidants (e.g., ascorbic acid); buffers (e.g., Tris-HCl); bulking agents (e.g., mannitol and glycine); chelating agents (e.g., EDTA); complexing agents (e.g., hydroxypropyl-beta-cyclodextrin); and the like.

Additional Embodiments

Figure 23:
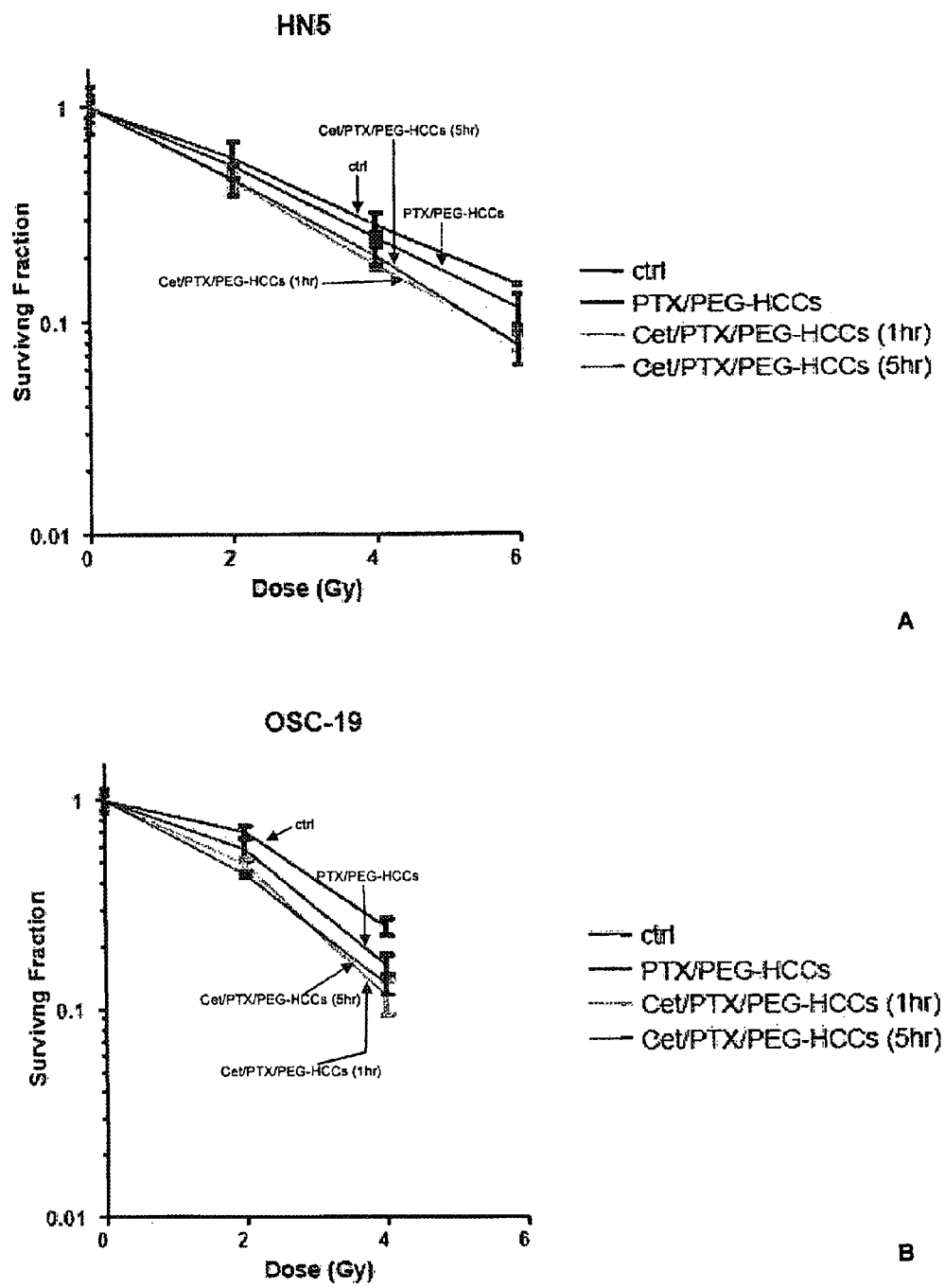
FIG. 23 shows results obtained when HN-5 cells (FIG. 23A) and OSC-19 cells (FIG. 23B) were co-treated with radiation and a therapeutic composition.

From the above disclosure, a person of ordinary skill in the art will recognize that the methods and compositions of the present disclosure can have numerous additional embodiments. For instance, in some embodiments, the treatment methods of present disclosure can further comprise the administration of radiation to a subject before, during or after administering the therapeutic composition. In fact, preliminary studies by Applicants have indicated that co-treatment of cancer cells with radiation and a therapeutic composition enhances the therapeutic composition's efficacy in killing the cancer cells. See FIG. 23.

Reference will now be made to more specific embodiments of the present disclosure and experimental results that provide support for such embodiments. However, Applicants note, that the disclosure below is for exemplary purposes only and is not intended to limit the scope of the claimed invention in any way.

EXAMPLES

Additional details about the experimental aspects of the above-described studies are discussed in the subsections below.

In general, the Examples below show that small (~20-80 μm-long cores) PEG-HCCs that are non-covalently associated with an active agent and targeting agent, such as a monoclonal antibody, effectively and selectively deliver the active agents in vitro and in vivo. Preliminary studies show that no toxicity has been observed for the PEG-HCCs, and the formulation is stable.

Without being bound by theory, Applicants envision that the potential of drugs, including the above-described therapeutic compositions, depends on the interaction characteristics in vitro and in vivo including pharmacokinetics (PK), tissue uptake and accumulation via biodistribution studies, stability in various matrices, and safety profile. Therefore, these parameters have been considered since they are important for the development of any new pharmaceutical, including the above-described therapeutic compositions.

Example 1

Characterization of HCCs and PEG-HCCs

Figure 1B:
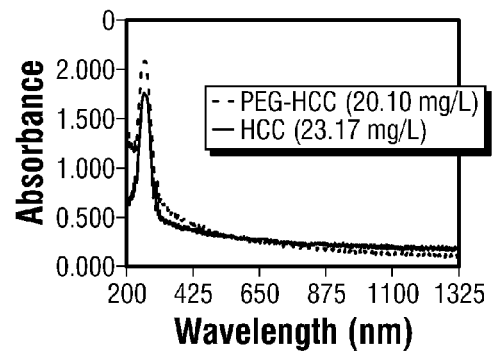
FIG. 1B shows UV-Vis spectra of both compounds with similar traces, indicative that their carbon cores are identical.
Figure 1C:
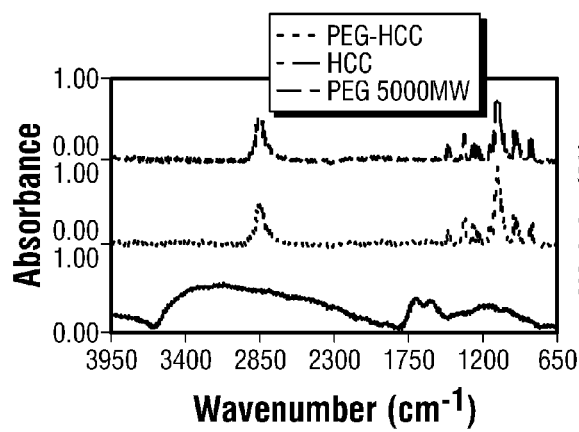
FIG. 1C shows FTIR of HCCs, PEG-HCCs and PEG alone, indicating the PEG polymer's presence in the PEG-HCCs. The HCC absorbencies are less intense.
Figure 1D:
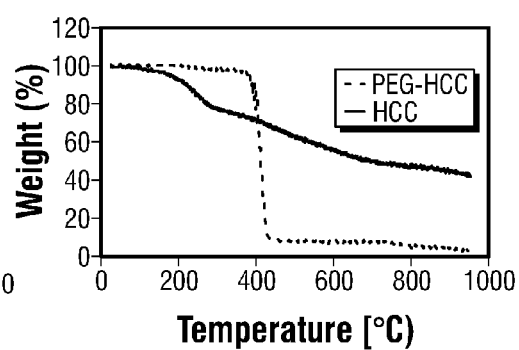
FIG. 1D shows thermogravimetric analysis (TGA), indicating a 58% weight loss for the HCCs and a 97% weight loss for the PEG-HCCs (25-950° C. at 10° C./min under Ar).
Figure 1E:
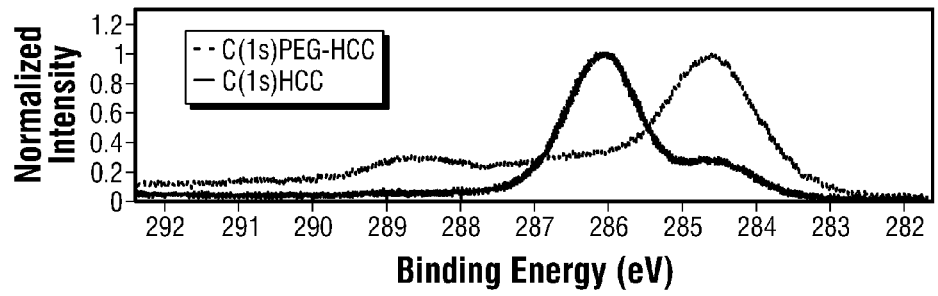
FIG. 1E shows the C(1s) portion of the XPS spectrum, reflecting both the high degree of oxidation for the HCCs (peaks>286 eV for C=O bonds) and the attachment of the PEG polymer for the PEG-HCCs (strong peak at 286 eV C—O bond).

The HCCs were prepared and characterized as described by Berlin et al. (*ACS Nano* 2010, 4, 4621-4636), and further by Lucente-Schultz et al. (*J. Am. Chem. Soc.* 2009, 131, 3934-3941), and further by Chen et al. (*J. Am. Chem. Soc.* 2006, 128, 10568-10571). HCC Characterization by atomic force microscopy (AFM) indicated that the HCCs were 20-80 nm long and 1 nm in diameter. See Berlin et al. for the characterization data. The studies also indicated that the HCCs possessed many oxidative groups on their sidewalls. In addition, X-ray photoelectron spectroscopy (XPS) demonstrated that the HCCs were highly oxidized. See FIG. 1E.

Example 2

Preparation and Characterization of PEG-HCCs

PEG-HCCs were prepared by coupling 5,000 MW methoxy(polyethylene glycol) amine (mPEG-NH2) to the carboxylic acids on the HCCs. The preparation method is illustrated in Scheme 1 below (and described in more detail in Berlin et al.), where only one of each functional group is shown for clarity:

Scheme 1
Preparation of PEG-HCC

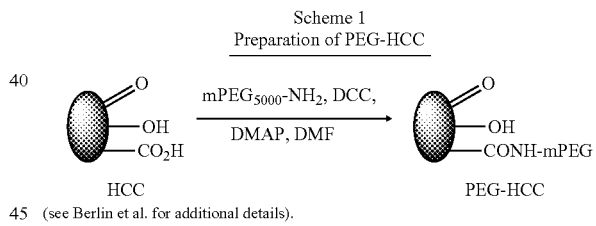

(see Berlin et al. for additional details).

The PEG-HCCs were purified by sequential dialysis in DMF and water. This was followed by passage through a PD-10 desalting column to remove any coordinated metals or unbound PEG. AFM indicated that the PEG-HCC particles had a greater height than the HCC particles (2.2 nm vs. 1.4 nm), reflecting the contribution from the attached polymer. The particles were water soluble. See Berlin et al. for AFM data.

Applicants have chosen to call these new molecules HCCs, as described by Berlin at al., rather than nanotubes of SWNTs because there are few or no radial breathing modes observed by Raman spectroscopy, indicating a loss of the contiguous tubular structure. See FIG. 1A. The UV-Vis and Raman spectroscopy are very similar for the PEG-HCCs and HCCs, indicating that, as expected, the HCC core remains unchanged by the attachment of the PEG polymer. See FIGS. 1A and 1B.

Fourier transform infrared spectroscopy (FTIR), XPS, and thermogravimetric analysis (TGA) all support the attachment of PEG to the HCCs. See FIGS. 1C-1E. The FTIR spectrum for the PEG-HCCs is very similar to the IR trace of PEG alone because the PEG-HCCs contain such an excess of the PEG repeat unit ($-CH_2CH_2O-$) relative to the HCC core. The XPS shows a dramatic increase in the C-0 signal (286 eV) for PEG-HCCs, as compared to HCCs, confirming PEG attachment. Finally, TGA indicates that the PEG-HCCs have a weight loss of 97%, while the HCCs have a weight loss of 58%. Applicants estimate that about 1 in 14 HCC carbons bear a PEG chain.

Example 3

Preparation of PTX/PEG-HCCs

Figure 2:
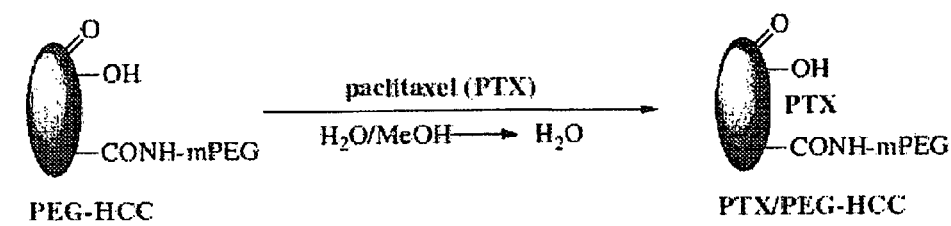
FIG. 2 illustrates the loading of PEG-HCCs with Paclitaxel (PTX) to form PTX/PEG-HCC.
Figure 2:
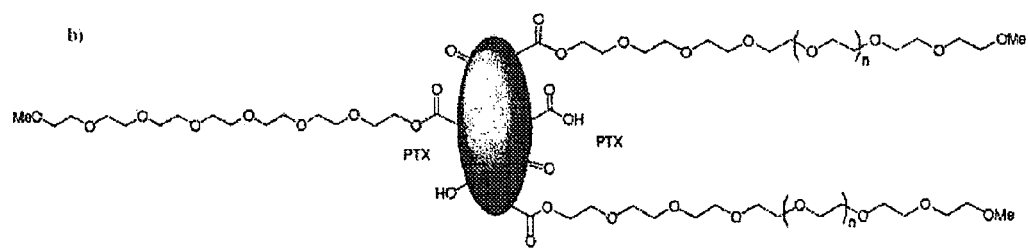
Figure 2:
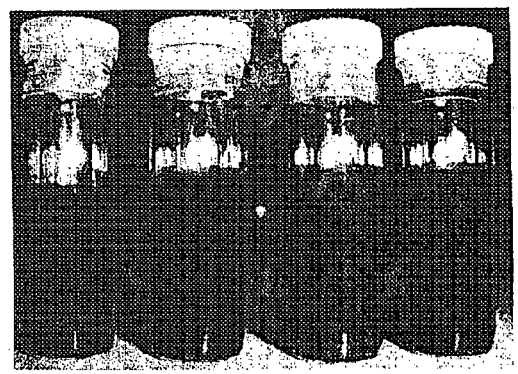

Here, Applicants show that PEG-HCCs are effective drug delivery vehicles when mixed with Paclitaxel. PEG-HCCs were loaded with PTX by dropwise addition of PTX in methanol (5 mg in 1 mL) to a rapidly stirring solution of PEG-HCCs in water (100 mg/L concentration of core HCCs, 5 mL). Next, the solution was bath-sonicated, concentrated to 3 mL by rotary evaporation (to remove the methanol), and then diluted back to the original volume (5 mL) with water. This provided a translucent solution of PTX non-covalently associated with PEG-HCCs (PTX/PEG-HCCs). See FIGS. 2A and 2B. As shown in FIG. 2C, the efficacy of the loading is easy to monitor, as PTX is insoluble in water. In other words, it is visually apparent if PTX is precipitating because the solution becomes a milky white color when the PTX is overloaded. Applicants have observed that the maximum loading concentration of PTX in the PEG-HCCs in the experiments performed to date is about 12 mg/mL.

Example 4

In Vitro and In Vivo Efficacy of PTX/PEG-HCCs

Figure 3A:
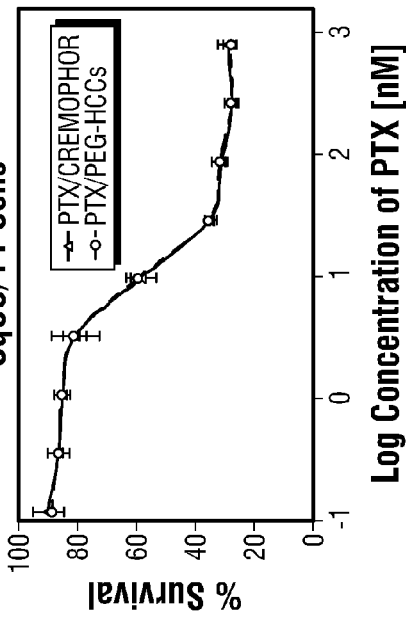
FIG. 3A also shows the inability of PEG-HCCs alone to kill cells (line with squares). Each graph represents an individual trial. Error bars are standard errors.
Figure 3B:
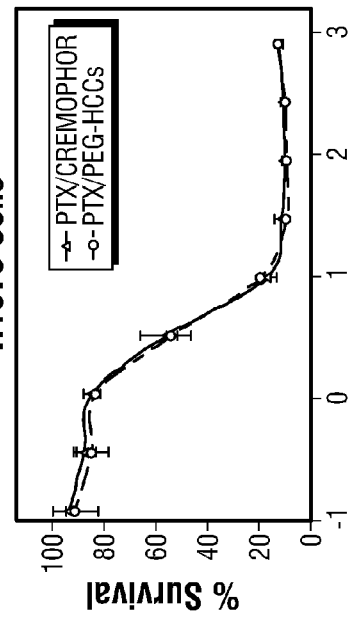
FIG. 3 illustrates the in vitro efficacy of PTX/PEG-HCCs in treatment of two head and neck cancer cell lines (FIGS. 3A and 3B) and two breast cancer cell lines (FIGS. 3C and 3D). The cell lines were treated with PTX/PEG-HCC (line with circles) and PTX/Cremophor (line with triangles).
Figure 3C:
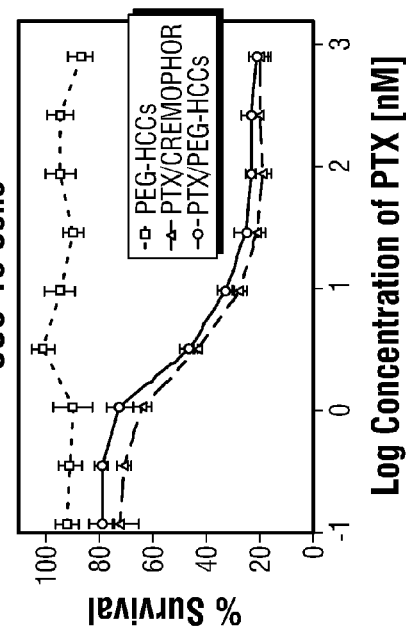
Figure 3D:
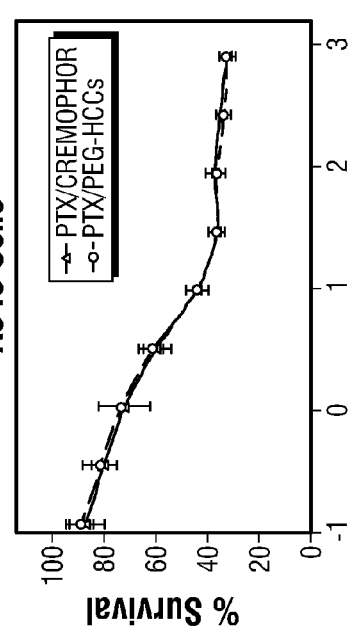

Two head and neck cancer cell lines (OSC-19, SQCCY1) and two breast cancer cell lines (A549, H1975) were treated for 3 days with PTX/PEG-HCCs, PEG-HCCs, and PTX/Cremophor (i.e., Taxol®). Subsequently, an MTT assay was performed to assess cell survival for the different concentrations of each compound. Applicants had previously investigated the in vitro toxicity of the PEG-HCCs and found that they are non-toxic at carbon core concentrations of less than 4 mg/L. For this reason, the PTX/PEG-HCCs were prepared such that the highest concentration of PTX used in the in vitro assay (500 nM) corresponded to a PEG-HCCs concentration of 3.6 mg/L. Duplicate trials with OSC-19 cells confirmed that the PEG-HCCs have no toxicity at concentrations of the carbon core less than 4 mg/L. See FIG. 3A (line with squares).

The results indicate that PTX/PEG-HCCs have the same cell-killing ability as Taxol® (i.e., PTX/Cremphor) at the same PTX concentrations in the cell lines studied. See FIGS. 3A-3D and Table 1. These studies also indicate that the PTX in the PTX/PEG-HCC matrix remains soluble and accessible. In comparison, when PTX is not fully solubilized and is then administered to cells, its cell killing ability is greatly decreased (data not shown).

TABLE 1

The $IC_{50}$ data for an average of three trials (96 wells/trial) and the standard deviations.

| A549 | OSC-19 | SQCCY1 | H1975 |
|---|---|---|---|
| 1.77 ± 0.37 | 1.94 ± 0.11 | 2.88 ± 0.43 | 1.69 ± 1.00 |
| 1.69 ± 0.31 | 1.87 ± 0.06 | 2.68 ± 0.53 | 1.63 ± 0.97 |

The stability of the PTX/PEG-HCCs formulation was evaluated over 20 weeks. See Table 2. Samples of PTX/PEG-HCCs and PTX/Cremophor were prepared and stored at 23° C. and 4° C., respectively. New OSC-19 cells were treated with each solution at each of the weeks indicated in Table 2. There was a small amount of week to week variation in the efficacy of both samples, likely due to the slightly different confluency of the cells, week to week. This is supported by the fact that whenever the $IC_{50}$ rose or fell for one sample, it also did so for the other sample. Indeed, in all cases, the PTX/PEG-HCCs formulation was as effective as the PTX/Cremophor formulation. In addition, Applicants did not observe any decline in the potency of either sample over the 20 week period.

TABLE 2

The stability of the PTX/PEG-HCCs evaluated in comparison to PTX/Cremophor over time.

| | $IC_{50}$ for OSC19 Cells [nM] | | | | | | | |
|---|---|---|---|---|---|---|---|---|
| Treatment | Wk 1 | Wk 2 | Wk 3 | Wk 4 | Wk 5 | Wk 6 | Wk 7 | Wk 20 |
| PTX/PEG-HCCs | 2.04 | 1.94 | 1.62 | 4.08 | 1.57 | 2.09 | 2.98 | 3.00 |
| PTX/Cremophor | 1.95 | 1.84 | 1.34 | 3.94 | 1.45 | 1.97 | 2.72 | 2.95 |

Figure 4:
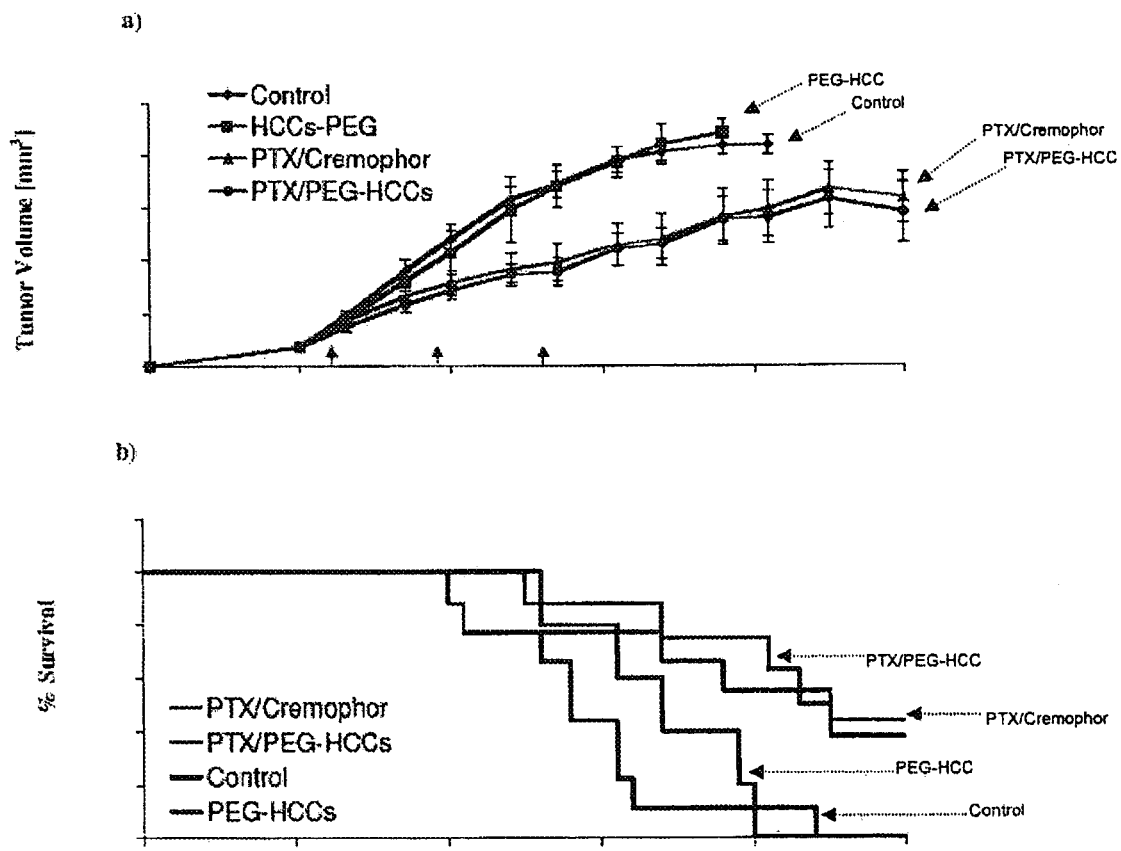
FIG. 4 shows results obtained from treatment of tumors in an orthotopic murine model of oral squamous cell carcinoma. Mice with orthotopically established oral tongue tumors were injected once weekly (at days 12, 19 and 26) with various treatments (control, PTX/Cremophor, PTX/PEG-HCCs, and PEG-HCCs).

Following the in vitro work, Applicants proceeded to evaluate the effectiveness of PTX/PEG-HCCs treatment on an orthotopic murine model of oral squamous cell carcinoma using the OSC-19 cell line. See FIG. 4. OSC-19 cells were injected into the tongues of 32 mice as described previously. See Myers et al., Clin. Cancer Res. 2002, 8, 293-8. After 12 days, the mice were randomized into four groups and treated weekly with either a saline solution (control, n=9), PTX/Cremophor (n=9), PTX/PEG-HCCs (n=9), or PEG-HCCs (n=5). For each of the PTX formulations, the dose was 8 mg PTX/kg. The PEG-HCCs were used at a concentration of 100 mg/L. The tumor sizes were measured twice per week using microcalipers. Tumor volume (V) was calculated using the formula V=(A)(B2)π/6 (A is the longest dimension of the tumor, and B is the dimension of the tumor perpendicular to A).

The mice were also weighed twice per week. The mice were euthanatized using carbon dioxide asphyxiation if they lost more than 20% of their pre-injection body weight or became moribund. The remaining mice were sacrificed at 50 days post-cell inoculation.

As a result, the PTX/Cremophor and PTX/PEG-HCCs treatments statistically decreased tumor volume. See FIG. 4A. In addition, the treatments increased survival relative to the control treatment. See FIG. 4B. The two PTX-treatments were statistically undistinguishable from each other.

Example 5

Radiolabeling of PEG-HCCs and PTX/PEG-HCCs

Since PEG-HCCs demonstrated efficacy in the delivery of a water insoluble cancer therapy drug (PTX), Applicants further evaluated the fate of these PEG-HCCs as nanocarriers. In particular, Applicants studied the biodistribution of PEG-HCCs with and without PTX by using $^{111}$In as a tracker in both healthy and orthotopically-implanted tumor mice. Indium was chosen because of its half-life of 2.8 days and ease of attachment to the PEG HCCs.

Figure 5:
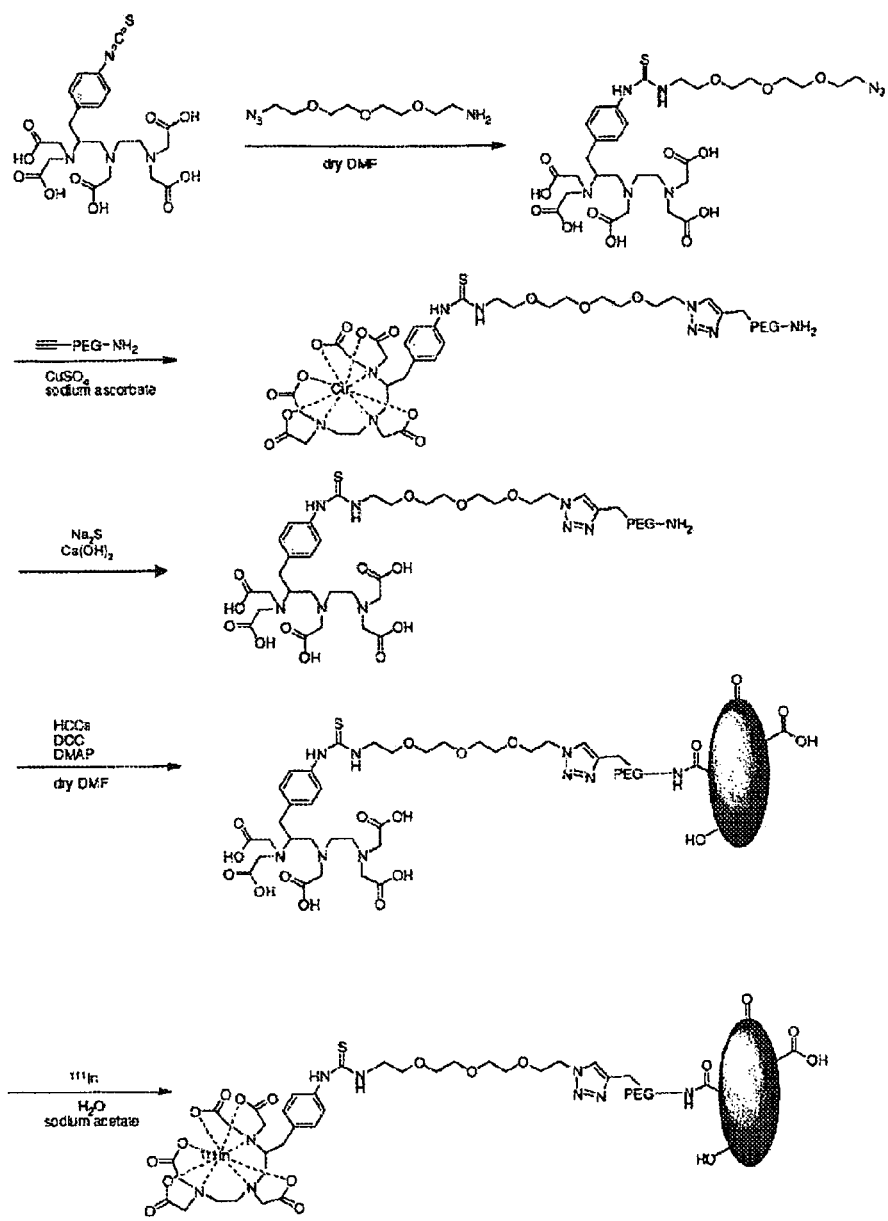
FIG. 5 outlines the steps in the synthesis of $^{111}$In-DTPA-PEG-HCCs for the biodistribution studies of PEG-HCCs

As illustrated in FIG. 5, diethylene triamine pentaacetic acid (DTPA) was used to functionalize HCCs in order to complex with $^{111}$In. DTPA isothiocyanate was coupled to an amino, azido functionalized PEG oligomer. The resulting product was joined to an amino, alkynyl functionalized 6,000 MW PEG chain using click chemistry, as commonly known. See van Dijk et al., *Bioconjugate Chem.* 2009, 20, 2001-2016. Treatment with Na$_2$S and Ca(OH)$_2$ removed any Cu bound to the DTPA. See Hong et al., *J. Hazard. Mater.* 2002, 94, 253-272.

The conjoined polymer was then coupled to the HCCs using standard peptide coupling conditions. See Montalbetti et al., *Tetrahedron* 2005, 61, 10827-10852. Small molecule contaminants were then removed using a size exclusion column. Next, the purified DTPA-PEG-HCCs were mixed with $^{111}$In, and any unbound $^{111}$In was removed by second size exclusion column to yield $^{111}$In-DTPA-PEG-HCCs. The binding efficiency of $^{111}$In to the DTPA-PEG-HCCs were then confirmed. The radiolabeled molecules were then used in the biodistribution studies described below.

Example 6

Biodistribution of PEG-HCCs and PTX/PEG-HCCs in Nude Mice 27 nude mice were administered 200 µL of $^{111}$In-DTPA-PEG-HCC at a concentration of 200 mg/L of PEG-HCCS via tail vein injections. Three mice were euthanized at each of the following time points: 0 (no treatment control), 0.5, 1, 3, 6, 18, 24, 48, 72, 96, and 120 h. A terminal blood sample was taken along with the heart, lungs, spleen, kidneys, liver, brain, and tongue. The radioactivity of each sample was determined using a gamma counter. The urine and feces were collected every 24 h, and all samples were shown to be quickly excreted through the urine and a smaller amount in the feces. There was no accumulation in the brain as expected.

Figure 6:
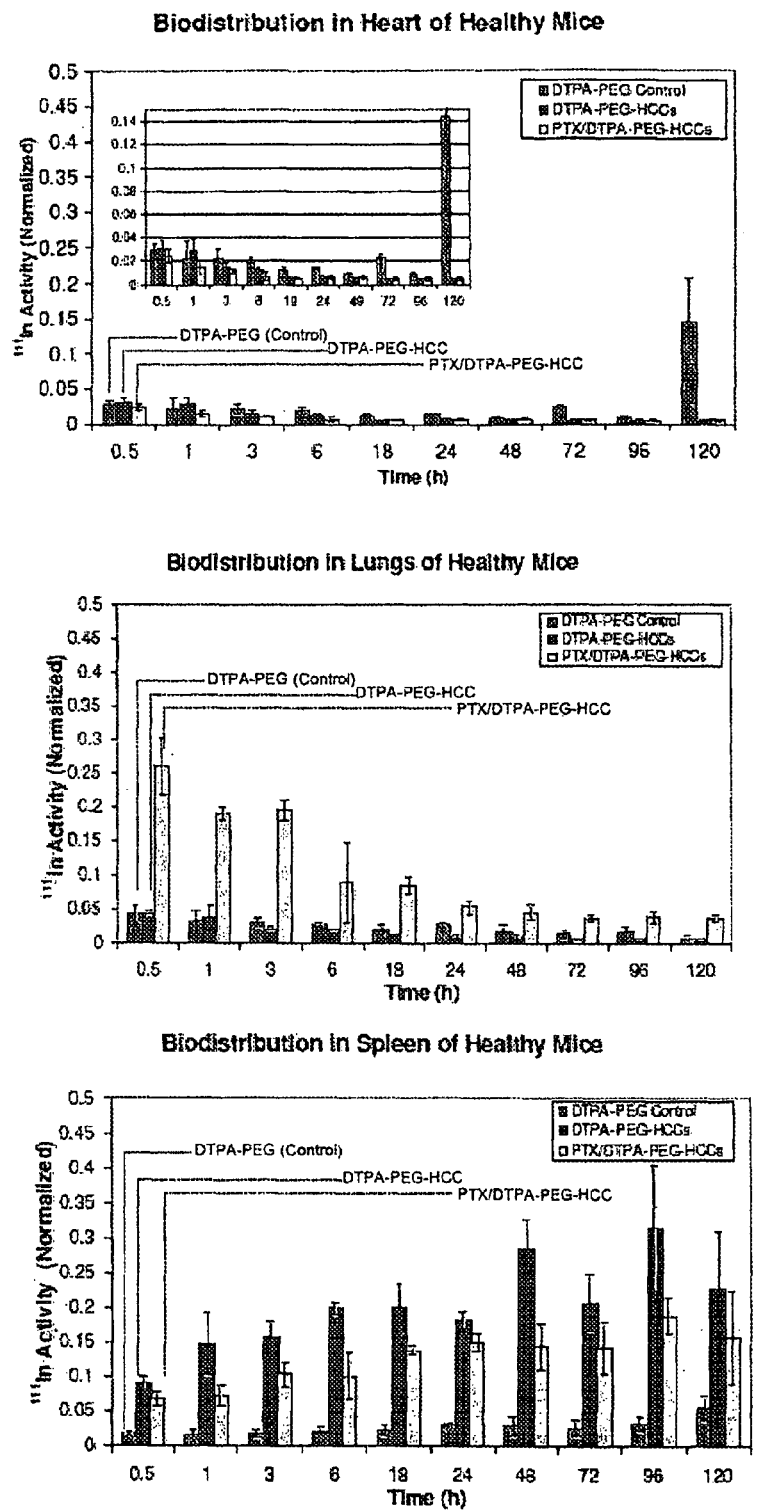
FIG. 6 shows the biodistribution of PTX/DTPA-PEG-HCCs in the heart (FIG. 6A), lungs (FIG. 6B), spleen (FIG. 6C), kidneys (FIG. 6D), liver (FIG. 6E), brain (FIG. 6F), tongue (FIG. 6G), blood (FIG. 6H), urine (FIG. 6I) and feces (FIG. 6J) of healthy nude mice. DTPA-PEG and DTPA-PEG-HCCs were used as controls.
Figure 6:
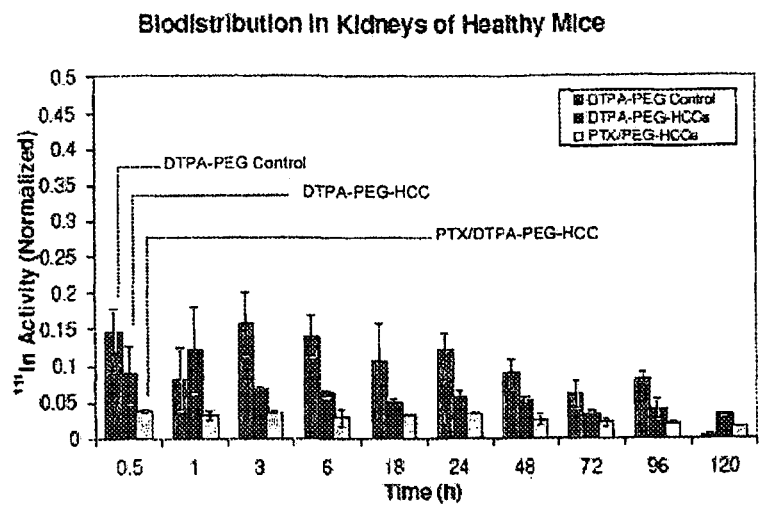
Figure 6:
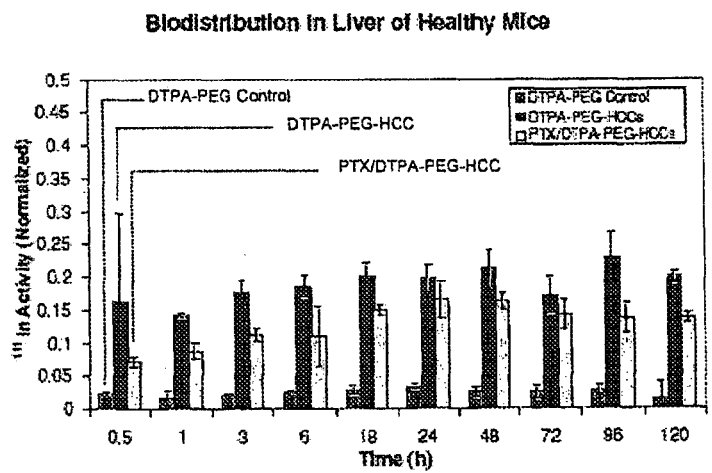
Figure 6:
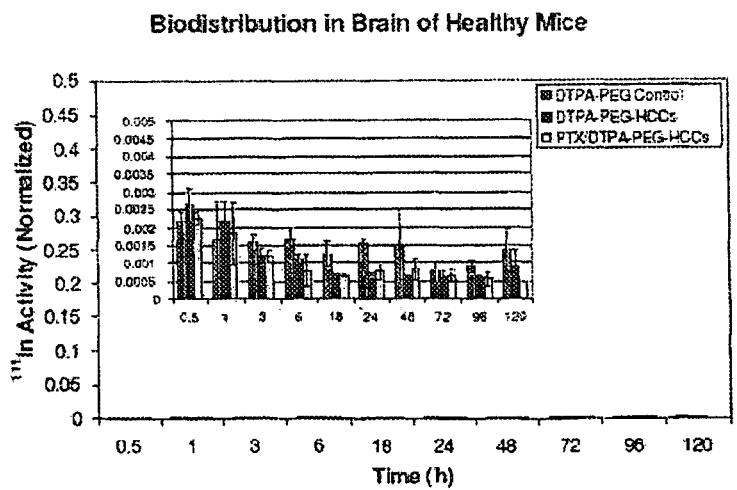
Figure 6:
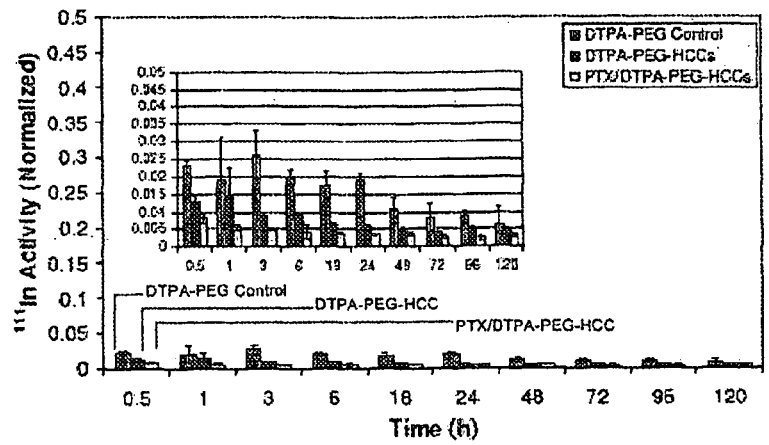
Figure 6:
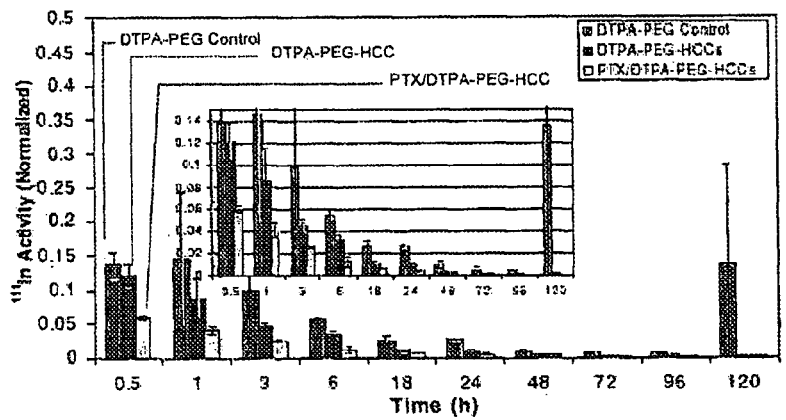
Figure 6:
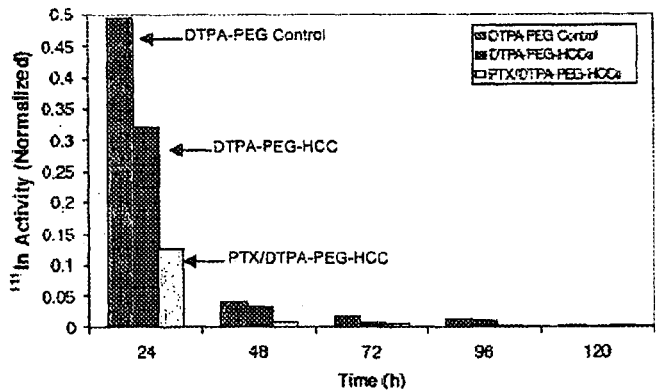
Figure 6:
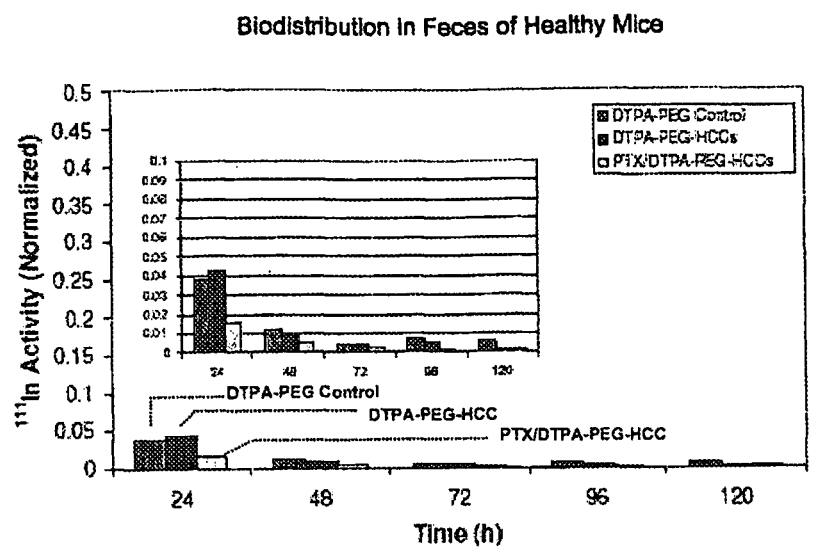
Figure 7A:
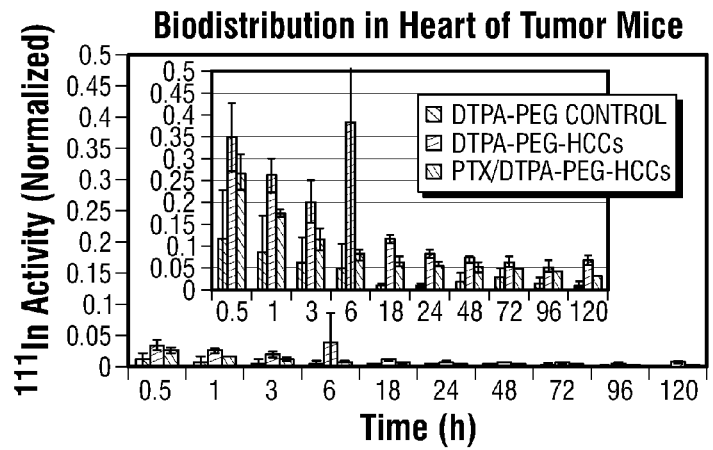
FIG. 7 shows the biodistribution of DTPA-PEG-HCCs and PTX/DTPA-PEG-HCCs in the heart (FIG. 7A), lungs (FIG. 7B), spleen (FIG. 7C), kidneys (FIG. 7D), liver (FIG. 7E), brain (FIG. 7F), tongue (FIG. 7G), blood (FIG. 7H), tumor (FIG. 7I), urine (FIG. 7J) and feces (FIG. 7K) of orthotopic tongue tumor mice.
Figure 7B:
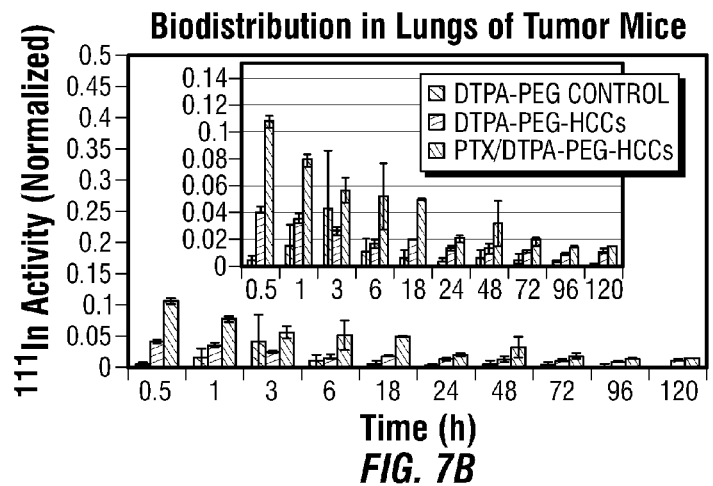
Figure 7C:
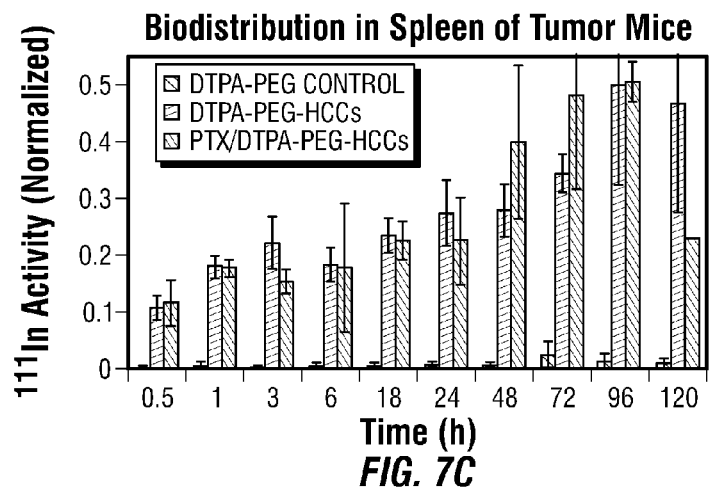
Figure 7D:
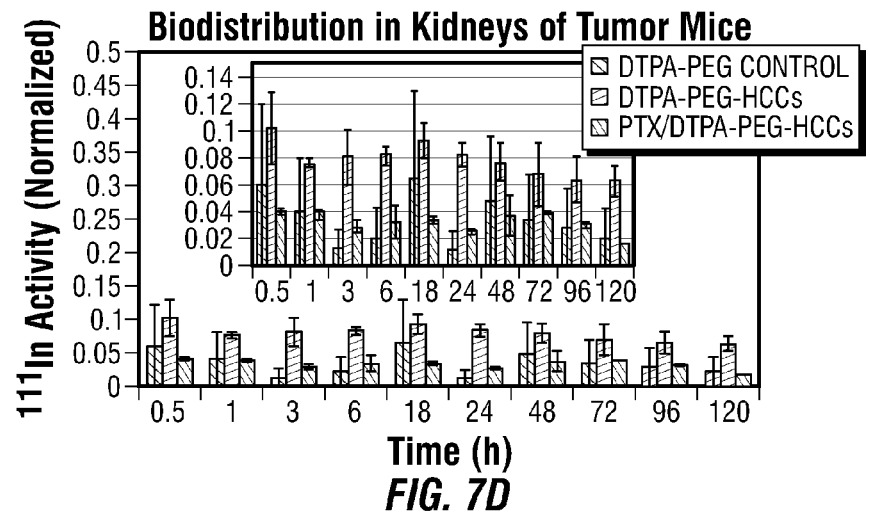
Figure 7E:
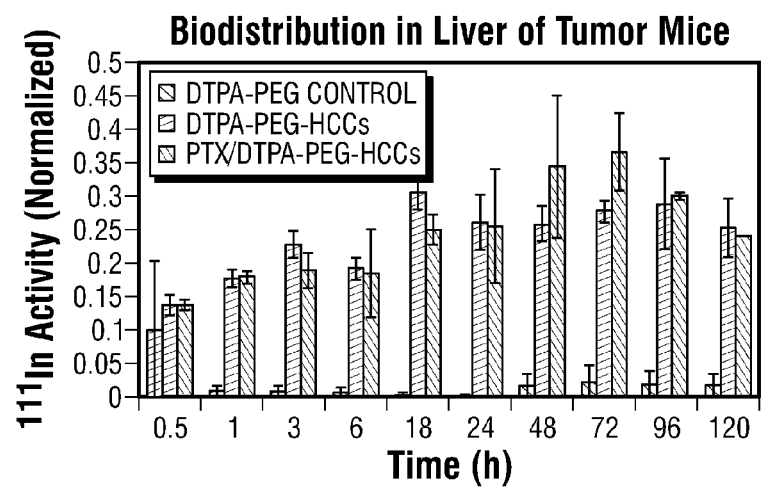
Figure 7F:
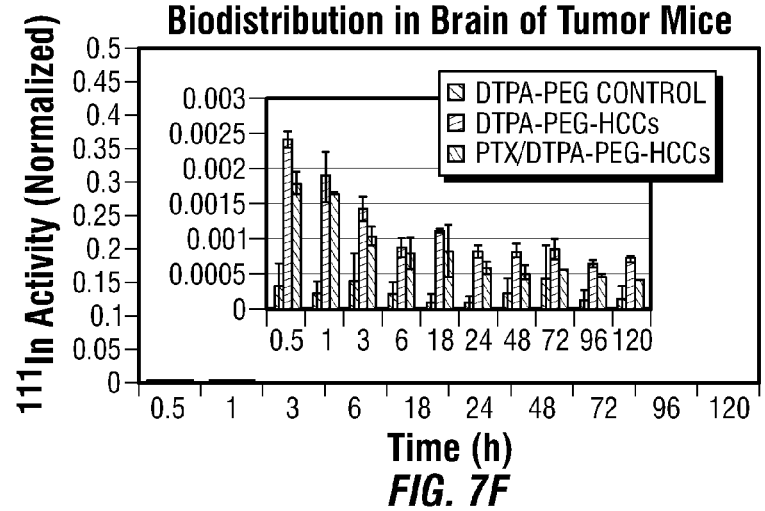
Figure 7G:
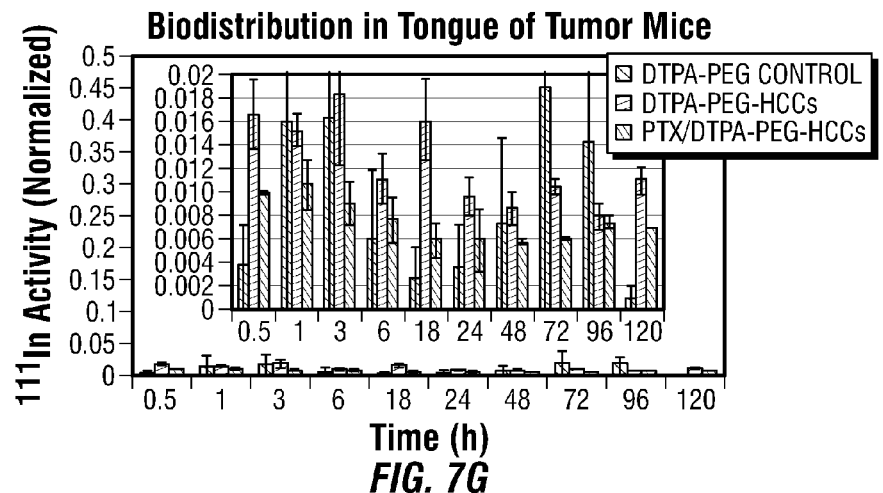
Figure 7H:
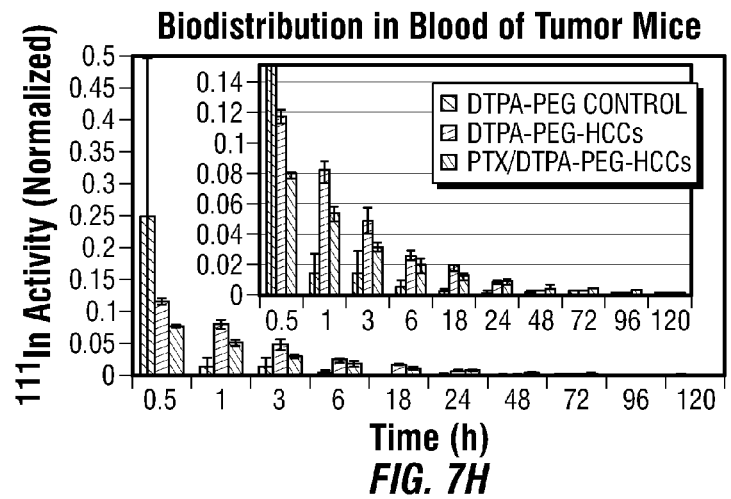
Figure 7I:
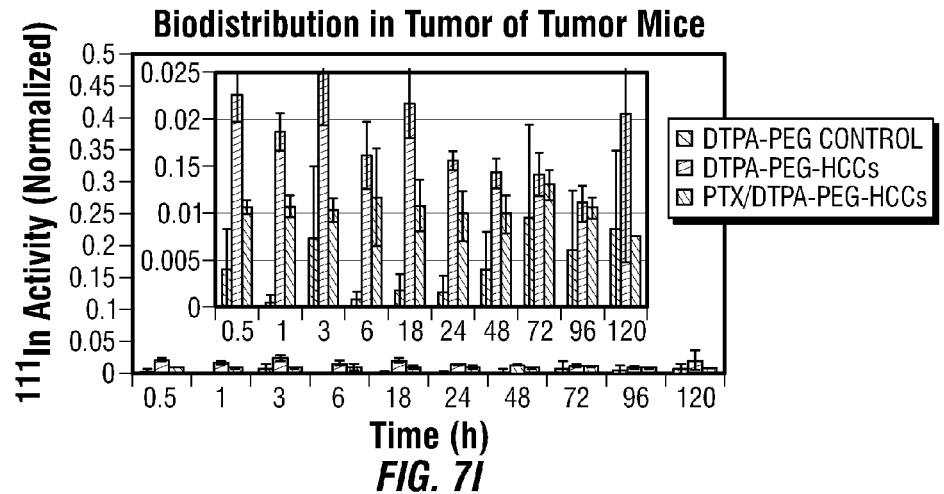
Figure 7J:
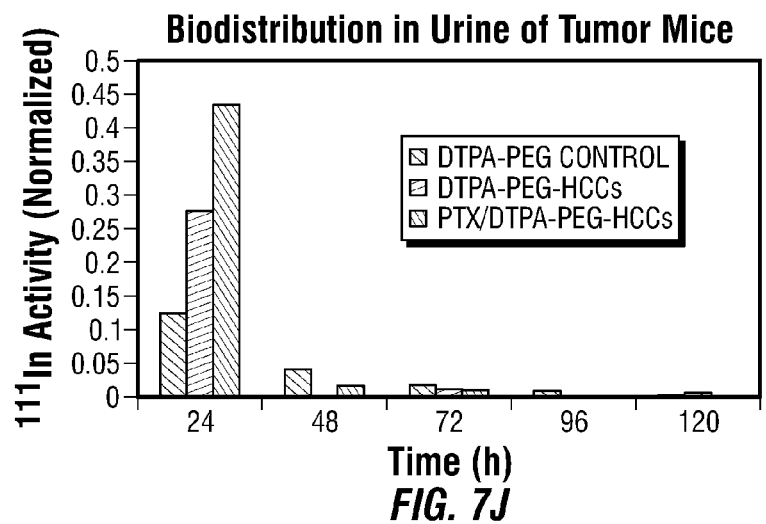
Figure 7K:
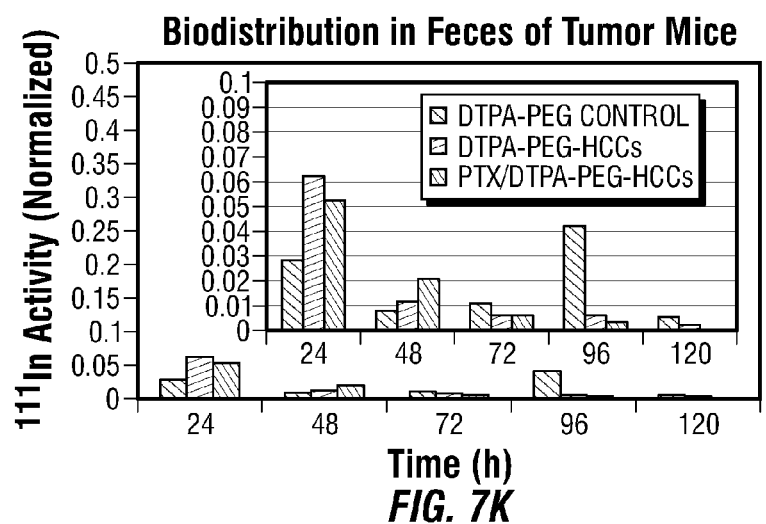

The results are shown in FIG. 6. The y-axis shown in the charts was normalized to the total organ radioactivity count divided by the organ's weight. This value was then divided by the initial radioactivity count injected in each mouse.

As shown in FIGS. 6C-6E, $^{111}$In-DTPA-PEG-HCCs accumulate in the spleen, liver, and kidneys. This pattern of accumulation is similar to other SWNT nanovectors. Applicants also observed that the PTX/PEG-HCCs were well distributed in highly vascular organs, such as the lungs, liver and kidneys. See FIGS. 6B and 6D-6E. This suggests that the distribution of PTX/PEG-HCCs is similar to Taxol®, which could lead to potential PEG HCC targeting.

Example 7

Biodistribution of PEG-HCCs and PTX/PEG-HCCs in Orthotopic Tongue Tumor Mice The same biodistribution study described in Example 6 was performed using an orthotopic tongue tumor mouse model. 30 mice were injected with 3×10$^5$ OSC-19 head and neck cancer cells one week prior to injection of $^{111}$In-DTPA-PEG, $^{111}$In-DTPA-PEG-HCCs or PTX/$^{111}$In-DTPA-PEG-HCCs. The rest of the biodistribution study was performed in the same manner as healthy mice show in Example 6.

FIG. 7 shows the distribution of $^{111}$In-DTPA-PEG-HCCs and PTX/$^{111}$In-DTPA-PEG-HCCs in orthotopic tongue tumor mouse. The biodistribution is very similar to the healthy mice with accumulation in the liver, spleen, and kidneys. See FIGS. 7C-7E. The PTX/PEG-HCC also accumulates in the lungs, as expected from the earlier results. See FIG. 7I3. Most importantly, the PEG-HCCs are capable of reaching the orthotopic tongue tumor. See FIGS. 7G and 7I.

Example 8

Targeted Delivery of Cet/PTX/PEG-HCCs

To study the efficacy of the therapeutic compositions of the present disclosure as targeted drug delivery agents, Applicants chose to associate Cetuximab with PTX/PEG-HCCs. By way of background, Cetuximab is an FDA-approved monoclonal antibody that selectively binds EGFRs, which are over-elevated on many tumor cell surfaces.

Figure 8:
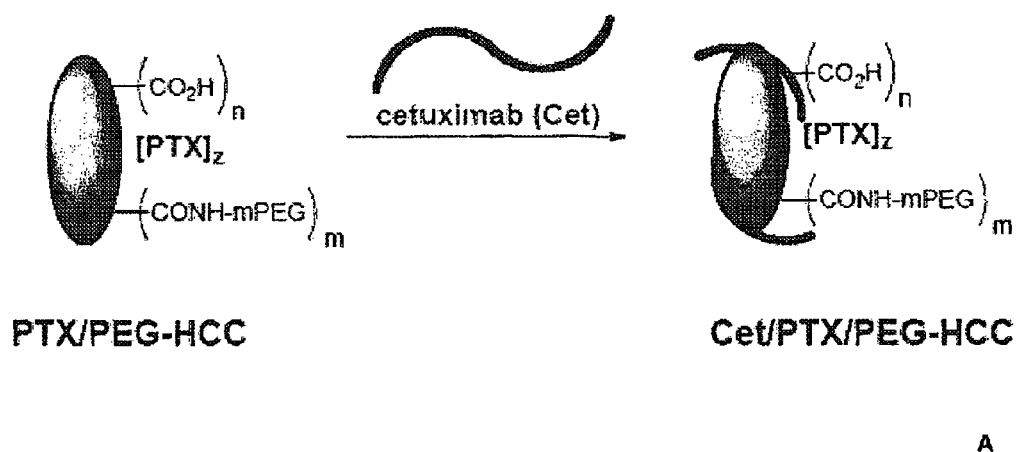
FIG. 8 illustrates the PTX/PEG-HCCs that were non-covalently wrapped with Cetuximab (Cet/PTX/PEG-HCCs).
Figure 8:
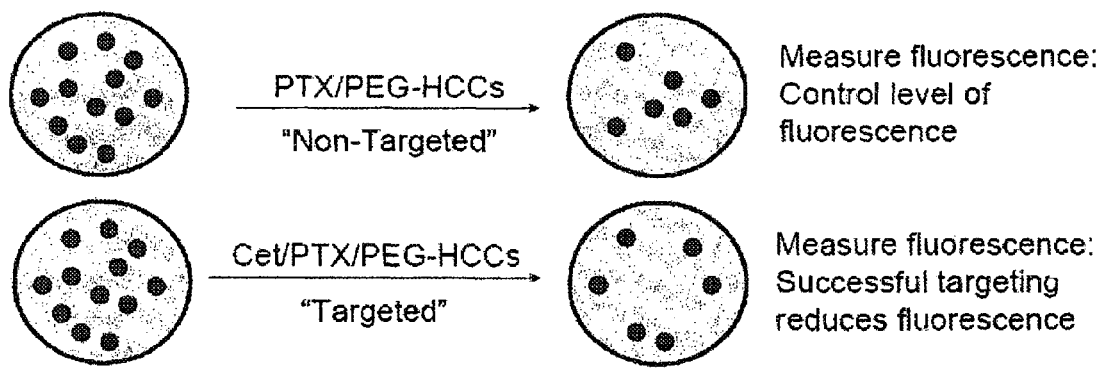
Figure 8:
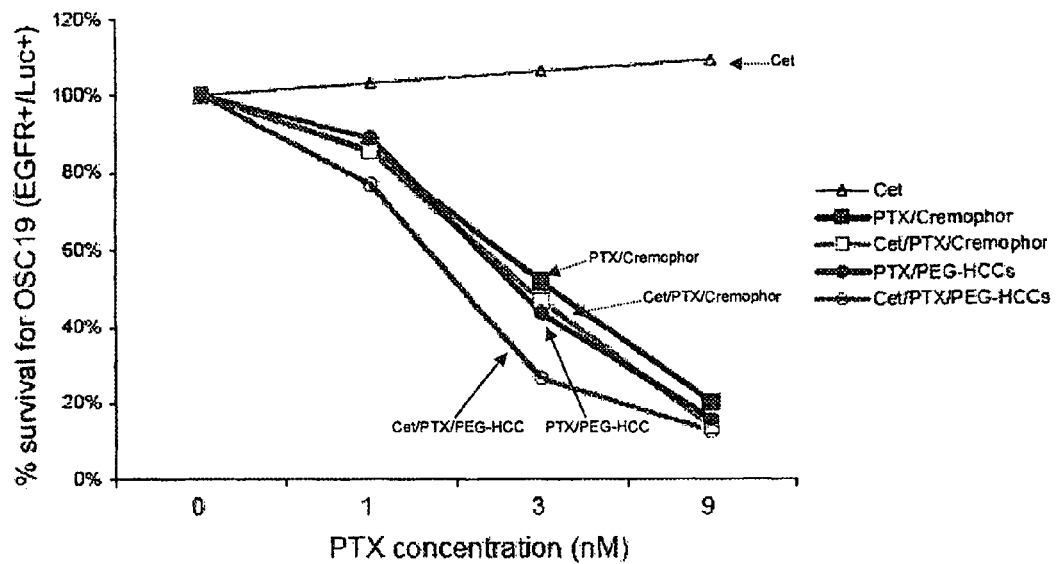
Figure 8:
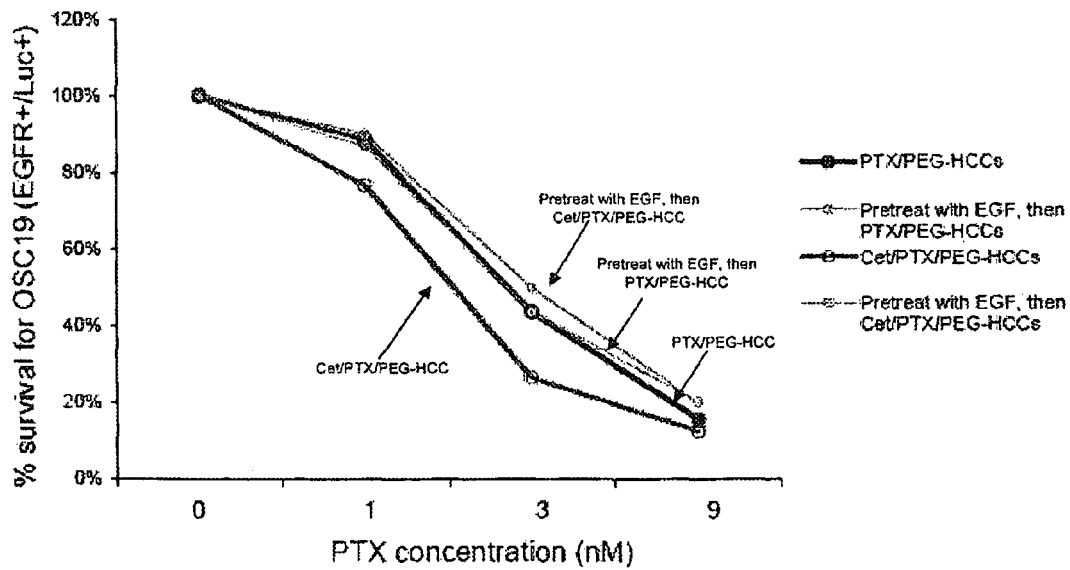

As illustrated in FIG. 8A, Cetuximab was mixed with PTX/PEG-HCCs to form Cet/PTX/PEG-HCCs. As shown, Cetuximab associated with the formed nanovector through non-covalent interactions.

To study the targeting effects of Cet/PTX/PEG-HCCs, OSC-19 cancer cells were first retrovirally infected with GFP and firefly luciferase gene as described in literature to form OSC19-Luc cells (EGFR$^+$/GFP$^+$). See Theodossis et al., *Cancer Research* 2005, 63, 1818-1821. Next, the OSC19-Luc cells were mixed with MCF-7 (EGFR$^-$/GFP$^-$) cancer cells and suspended in DMEM prior to the treatment.

Applicants envisioned that after treating cells with EGFR-targeted nanovectors, the bioluminescence intensity from luciferase could be quantified by using an IVIS 200 Imaging System (Xenogen). Applicants also envisioned that if EGFR-targeted PTX/PEG-HCCs could target OSC19-Luc cells, the measured bioluminescence would be lower than that with control and untargeted PTX/PEG-HCCs. See FIG. 8B.

As shown in FIG. 8C, Cetuximab alone had no effect on the cells. PTX/PEG-HCCs and PTX/Cremophor EL showed the same level of cell killing. Mixing Cetuximab with PTX/Cremophor EL had no effect. However, mixing Cetuximab with the PTX/PEG-HCCs resulted in significantly more killing of the OSC19 cells. In general, when EGFR$^+$ and EGFR$^-$ cells were co-cultured, use of the targeted formulation (Cet/PTX/PEG-HCC) resulted in greater cell death for the EGFR$^+$ cells compared to when the non-targeted formulation (PTX/PEG-HCC) or PTX/Cremophor formulations were used.

To confirm whether the increase in EGFR$^+$ cell killing was the result of the targeting effect from Cet/PTX/PEG-HCCs, the mixed cells of OSC-19-Luc (EGFR$^+$) and MCF-7 (EGFR$^-$) were pretreated with EGF before treatment. As shown in FIG. 8D, pretreatment with EGF had no effect on treatment with PTX/PEG-HCCs. However, the pretreatment eliminated the increased OSC19 killing by Cet/PTX/PEG-HCC nanovectors. This supports the hypothesis that Cet/PTX/PEG-HCC acts primarily through an EGFR targeting effect.

Figure 9:
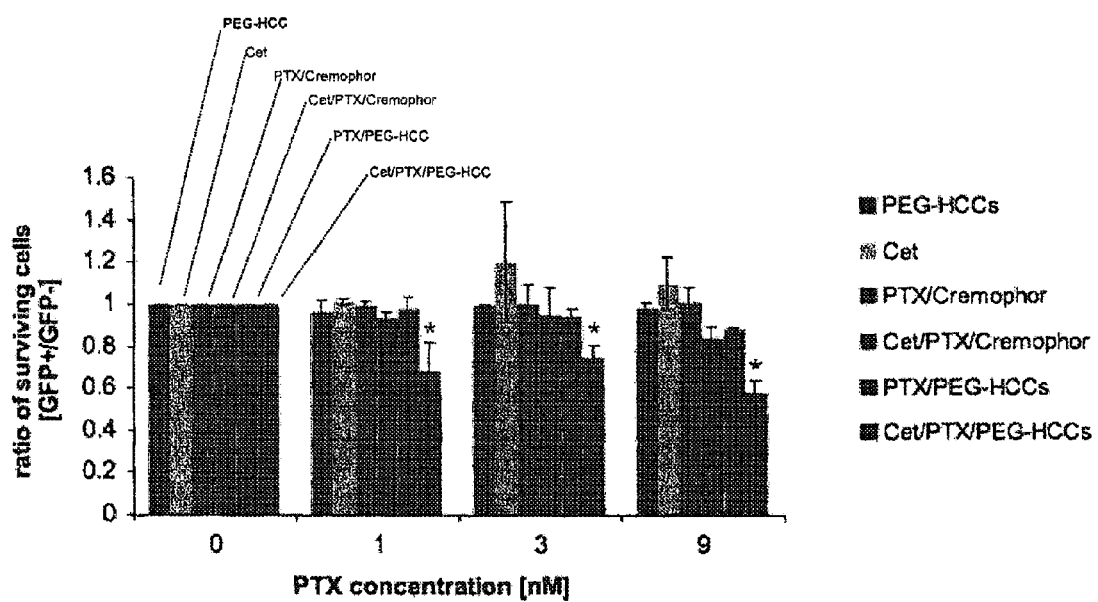
FIG. 9 shows flow cytometry experimental results obtained from the in-vitro targeting of Cet/PTX/PEG-HCCs.

Flow cytometry was also used to evaluate the ability of Cet/PTX/PEG-HCCs for targeted delivery of PTX to EGFR$^+$ cells. As shown in FIG. 9, successful EGFR targeting was indicated by a lower ratio (GFP+/GFP−) for the Cet/PTX/PEG-ICCs, as compared to other treatments.

Example 9

In Vitro Stability of Cet/PTX/PEG-HCCs

Figure 10:
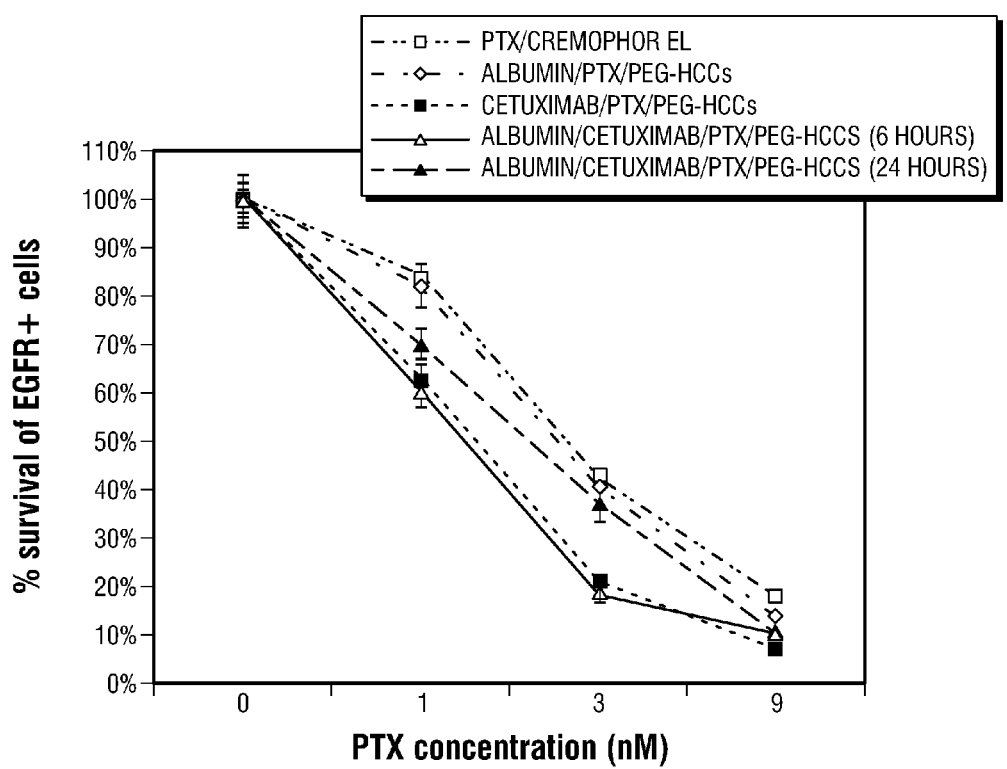
FIG. 10 shows in vitro experimental results relating to the stability of Cetuximab binding to PEG-HCCs in the presence of exogenous proteins.

When administered in vivo, the Cet/PTX/PEG-HCCs will be in the presence of many other proteins in the blood stream. In order to test the stability of Cetuximab binding to the PEG-HCCs in the presence of exogenous proteins, the Cet/PTX/PEG-HCCs were mixed with albumin for 6 hours prior to cell treatment. As shown in FIG. 10, no effect was observed. However, mixing for 24 hours eliminated some of the targeting effect.

Figure 11:
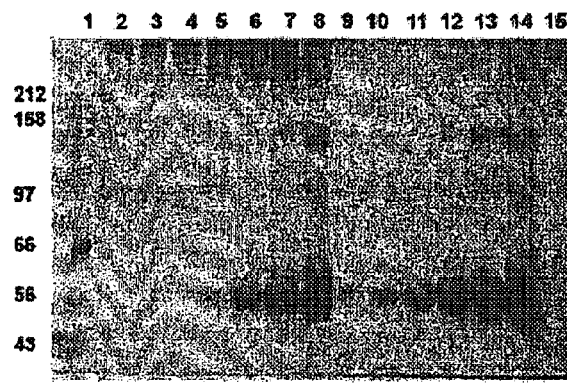
FIG. 11 shows a 7% SDS-PAGE gel loaded with free Cetuximab and Cet/PEG-HCC complexes with different concentrations of Cetuximab (from 0.03125 mg/ml to 1.0 mg/ml) to study the binding efficiency between Cetuximab and PEG-HCCs. The concentration of PEG-HCCs was held constant at 0.1 mg/ml.

To better understand the interaction between Cetuximab and PEG-HCCs, an SDS-PAGE gel electrophoresis was performed on free Cetuximab and Cet/PEG-HCCs with different Cetuximab concentrations. The results are shown in FIG. 11. The bands at 50 kDa correspond to the heavy chain of Cetuximab. The bands at 150 kDa correspond to the unreduced Cetuximab. Comparing lanes 2 and 3 with lanes 9 and 10, it is clear that Cetuximab at concentrations of 0.062 mg/ml and below are strongly bound to the PEG-HCCs (0.1 mg/ml).

Figure 12:
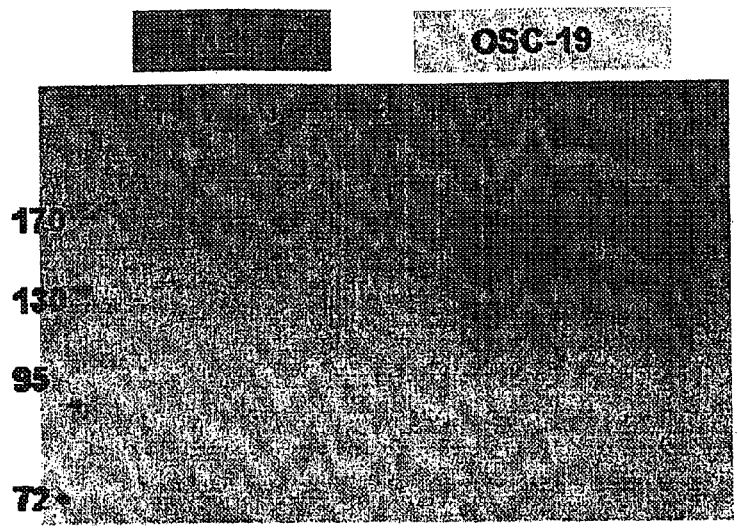
FIG. 12 shows results obtained from various immunoprecipitation studies.
Figure 12:
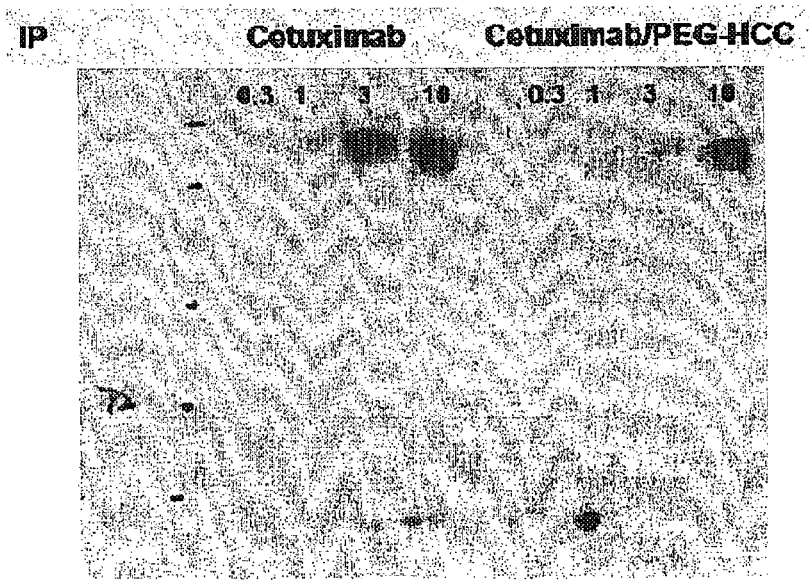

Applicants also sought to compare the EGFR binding efficacy of Cet/PEG-HCCs with free Cetuximab. Thus, immunoprecipitation (IP) was performed using protein extracts from EGFR$^-$ cells (MCF-7) and EGFR$^+$ cells (OSC-29) to evaluate such binding efficiencies. As shown in FIG. 12A, Applicants found that both Cet/PEG-HCCs and Cetuximab only selectively pull down a ~170 kDa protein from EGFR$^+$ cells. This protein was identified as EGFR by staining with an anti-EGFR antibody (Santa Cruz sc-03). EGFR does not seem to irreversibly bind to PEG-HCCs under these experimental conditions, as no EGFR was observed at the very top of the gel. In addition, Applicants did not observe any differences in IP efficiency between free Cetuximab and Cet/PEG-HCCs.

However, in the above-described experiment, it was difficult to tell the difference in EGFR binding between the positive control lane (2 μg of Cetuximab, "PC" lane) and the test case with less Cetuximab (0.359 μg of Cetuximab, lane 2). Thus, Applicants performed another IP experiment with several lesser amounts of EGFR. As shown in FIG. 12B, the experimental results demonstrate that less EGFR was pulled down by Cet/PEG-HCC than free Cetuximab.

Example 10

In Vivo Efficacy of Cet/PTX/PEG-HCCs

The same procedure outlined in Examples 6-7 were used to demonstrate the in-vivo efficacy of Cet/PTX/PEG-HCCs. Briefly, mice were pre-injected with two different tumor cell lines, OSC-19 (FIG. 13) and Fadu (FIG. 14). After one week, the mice were injected at various time intervals with various treatments (saline, Cetuximab, Cet/PEG-HCCs, PTX/Cremophor, Cet/PTX/Cremophor, and Cet/PTX/PEG-HCCs). Thereafter, tumor volume was measured twice weekly with calipers.

Figure 13A:
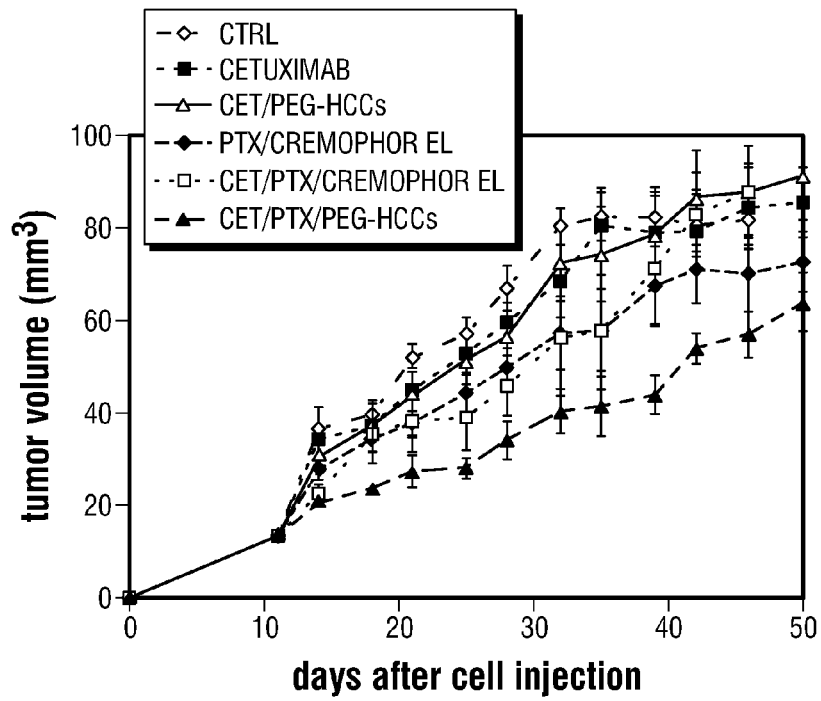
FIG. 13A shows the change in tumor volume of the mice after treatment. Tumor volume was measured twice weekly. Error bars are standard errors. A paired t-test was used to compare the differences in tumor volume.
Figure 13B:
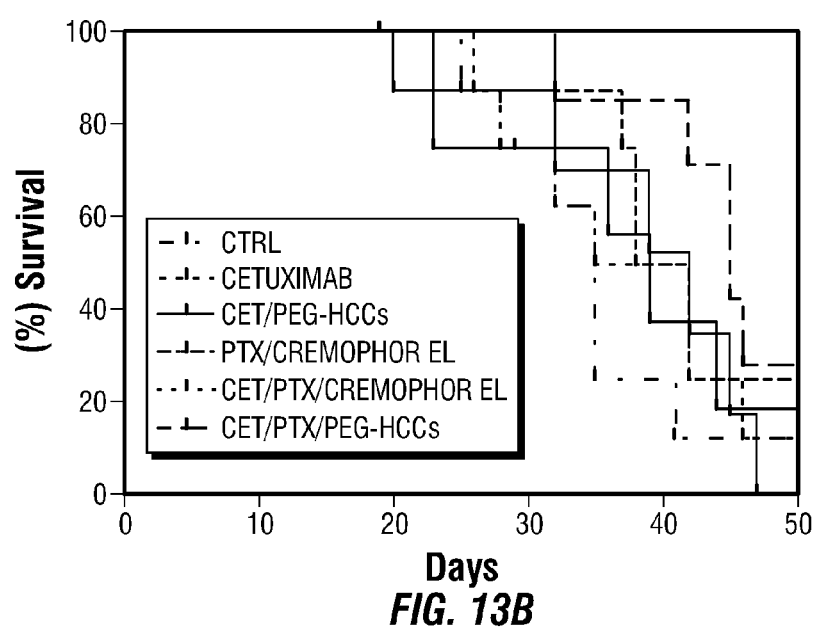
FIG. 13B shows the animal survival rate over 50 days, as analyzed by the Kaplan-Mieir method and compared with log-rank tests.
Figure 14A:
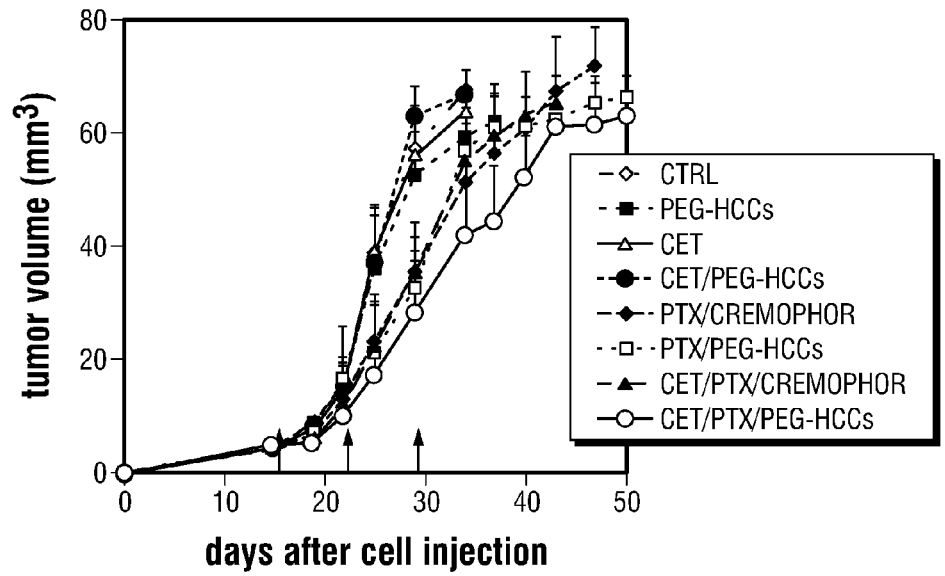
FIG. 14A shows the change in tumor volume of the mice after treatment. Tumor volume was measured twice weekly. Error bars are standard errors. A paired t-test was used to compare the differences in tumor volume. The arrows denote the days of injection.
Figure 14B:
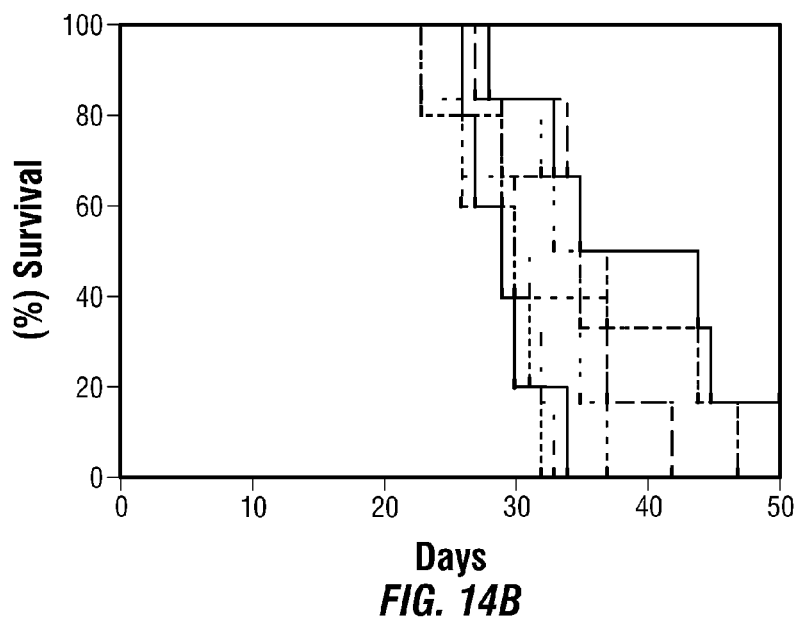
FIG. 14B shows the animal survival rate over 50 days, as analyzed by the Kaplan-Mieir method and compared with log-rank tests.

As shown in FIGS. 13A and 14A, Cet/PTX/PEG-HCCs statistically decreased tumor volume more than the other treatments in both mouse tumor models. Additionally, as shown in FIGS. 13B and 14B, the groups treated with Cet/PTX/PEG-HCCs had the greatest number of surviving animals 50 days after treatment.

Figure 15:
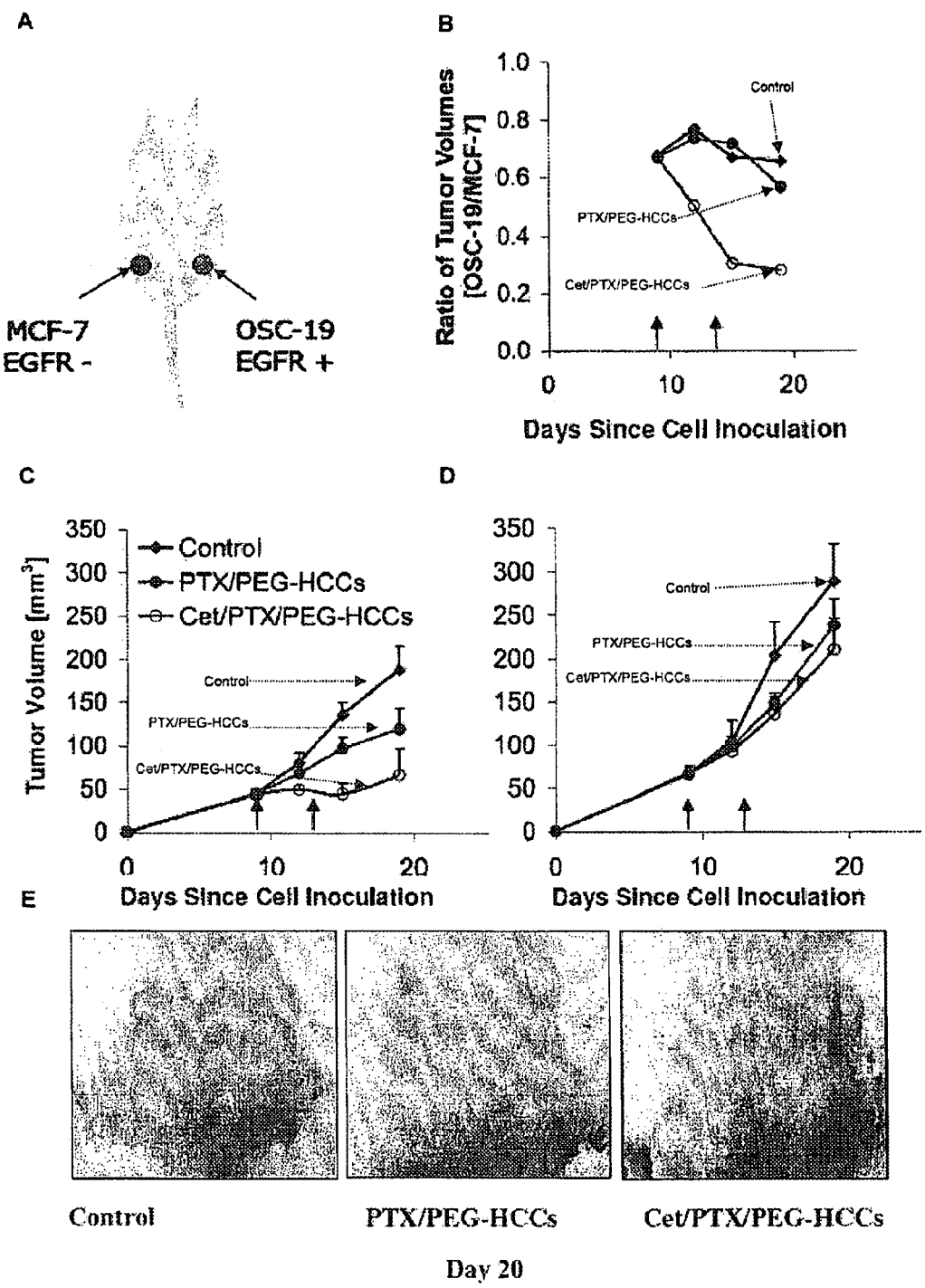
FIG. 15 shows results obtained from treatment of OSC-19 and MCF-7 tumor cells in mice.

As illustrated in FIG. 15A, a joint flank model was also used to study the in vivo efficacy of Cet/PTX/PEG-HCCs. In this model, nude mice were injected in the hindquarters with OSC-19 cells (EGFR$^+$) on one side and MCF-7 (EGFR$^-$) cells on the other side. It was necessary to use matrigel to get the MCF-7 cells to grow suitably. After 9 days, both tumors had grown a significant amount. Thereafter, the animals were randomized and treated with saline (Control), PTX/PEG-HCCs or Cet/PTX/PEG-HCCs. Treatments were given again at day 16.

As illustrated in FIGS. 15B-15E and observed by Applicants, the targeted formulation dramatically reduced the OSC-19 tumors; but not the MCF-7 tumors. This finding confirms that Cet/PTX/PEG-HCCs selectively deliver PTX to EGFR$^+$ cells.

Example 11

In Vitro Efficacy of PTX/PEG-HCCs

Figure 16:
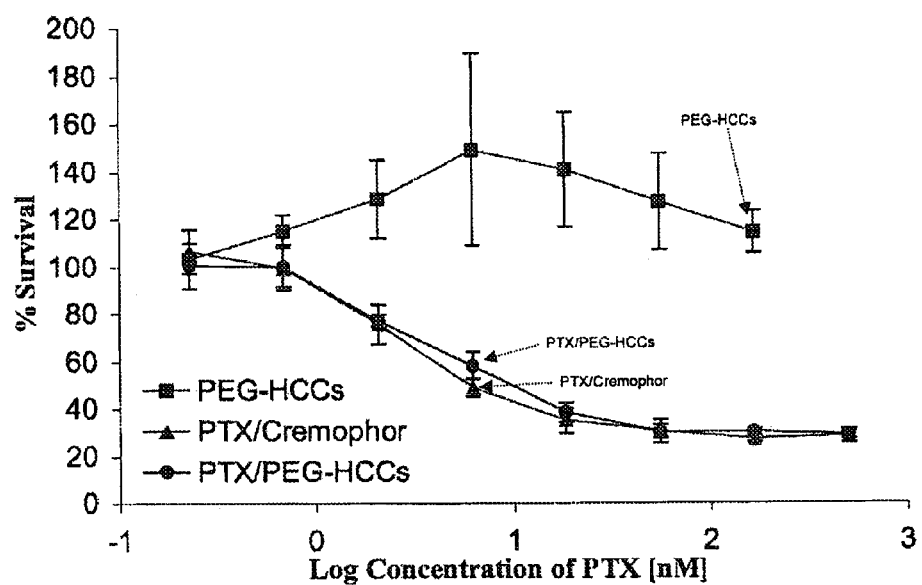
FIG. 16 shows the in vitro efficacy of PTX/PEG-HCCs on normal cells. HOK16B normal keratinocyte cells were treated with PEG-HCCs (line with squares), PTX/PEG-HCCs (line with circles), and PTX/Cremophor (line with triangles).

Applicants also treated a non-cancerous keratinocyte cell line (HOK16B) with PEG-HCCs, PTX/Cremophor, and PTX/PEG-HCCs. As shown in FIG. 16, treatment of the cells with PEG-HCCs had no effect. However, treatment with PTX/PEG-HCCs and PTX/Cremophor were equally effective. These findings are consistent with Applicants' prior results for the cancerous cell lines.

Example 12

Comparative Efficacy of PEG-CNMs

In another set of experiments, Applicants compared the targeted drug delivery capabilities of three different PEGylated carbon nanomaterials (PEG-CNM): PEG-HCCs, PEGylated graphite oxide nanoribbons (PEG-GONR) and PEGylated oxidized carbon black (PEG-OCB). PEG-GONRs were made as described in Higginbotham et al. (*ACS Nano* 2010, 4, 2059-2069) and Kosynkin, D. et al. (*Nature* 2009, 458, 872-826). PEG-OCBs were made as described, in Berlin et al. ("Engineered nanoparticles for hydrocarbon detection in oil-field rocks" *Energy & Environmental Sciences* (accepted for publication)).

In this assay, two different cell lines, OSC-19 (EGFR$^+$/Luc$^+$) and MCF-7 (EGFR$^-$/Luc$^+$) were co-cultured. The co-cultures were treated with PTX/Cremophor EL, PTX/PEG-CNM, or PTX/PEG-CNM's with various ratios of Cetuximab. Successful targeted drug delivery is indicated by a' reduction in the survival of the OSC-19 cells, as measured by luciferase activity.

Figure 17A:
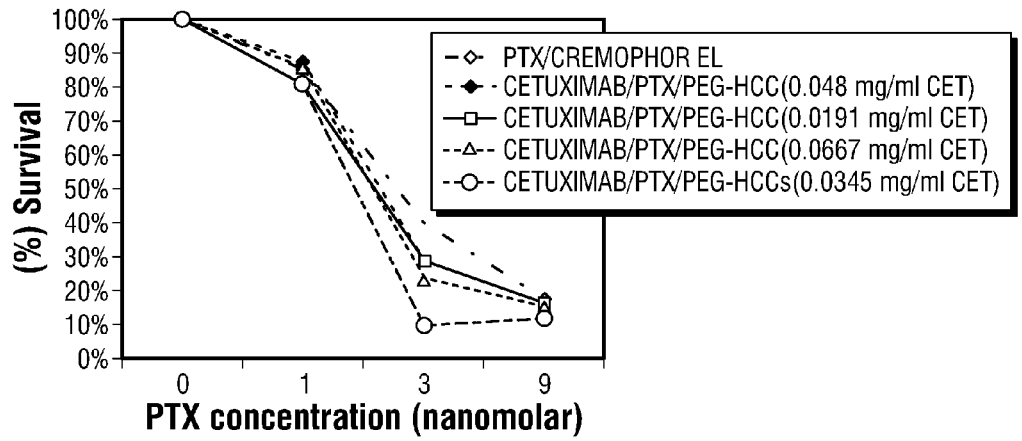
FIG. 17A shows that the targeting of the drug delivery improves as the ratio of Cetuximab to PTX/PEG-HCCs is varied.
Figure 17B:
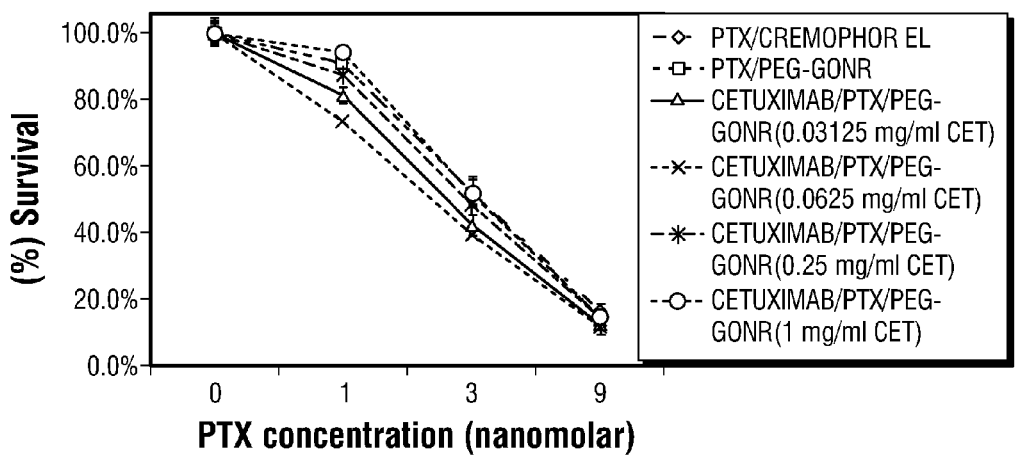
FIG. 17B shows that the targeting of the drug delivery improves as the ratio of Cetuximab to PTX/PEG-GONRs is varied.
Figure 17C:
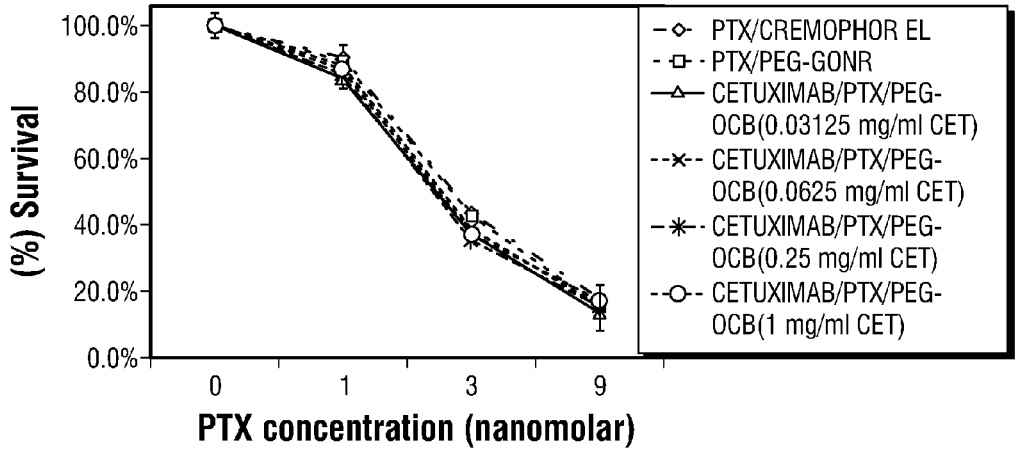
FIG. 17C shows no changes in improvement of the drug delivery as the ratio of Cetuximab to PTX/PEG-OCBs is varied.

As shown in FIGS. 17A-17C, Applicants found that the PEG-HCCs were the most effective PEG-CMNs. The results also indicated that the PEG-GONRs demonstrated modest targeting efficacy. See FIG. 17B. However, Applicants did not observe less optimal results when they used PEG-OCBs. See FIG. 17C.

Example 13

Treatment of Oxidative Stress

As set forth previously, Applicants also envision that the therapeutic compositions and methods of the present disclosure can be used to treat oxidative stress. By way of example and background, oxidative stress is a prominent feature of mild traumatic brain injury (mTBI), especially when accompanied by secondary insults such as hemorrhagic hypotension. Antioxidant therapies have had limited success in treating mTBI. Without being bound by theory, one likely reason for this failure can be that these agents are short acting and only minimally effective in-vivo.

Furthermore, studies suggest that time of resuscitation is a potential time point for treatment of TBI, as there is a major peak of superoxide produced following resuscitation. Since there is clinical access to the patient at this point, it is potentially feasible to administer an antioxidant therapy along with agents employed for resuscitation.

Figure 18:
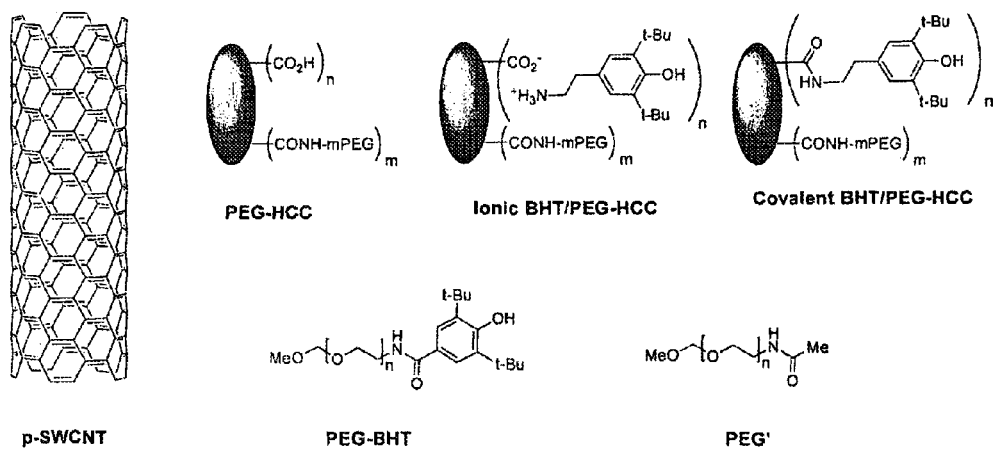
FIG. 18 shows the structures of various carbon nanomaterials that are potent antioxidants (and the appropriate controls).

Initially, Applicants identified carbon nanomaterials as potent antioxidants. See FIG. 18. Applicants hypothesized that these materials can be potent antioxidants in vivo, with a long duration of action. Specifically, Applicants envision that four carbon nanomaterials show potential as antioxidants: pluronic wrapped single walled carbon nanotubes (p-SWNT), PEG-HCCs, butylated hydroxytoluene ionically bound to PEGylated hydrophilic carbon clusters (Ionic BHT/PEG-HCC), and BHT covalently bound to PEG-HCCs.

In fact, Applicants have confirmed the efficacy of various nanomaterials as antioxidants through an oxygen radical absorbency capacity (ORAC) assay using a chemical source for the oxygen radical (α,α'-azodiisobutyramidine dihydrochloride). See Table 3. This assay identified the pluronic wrapped SWNTs and ionic BHT/PEG-HCCs as promising nanomaterials for in vivo work. Applicants also developed conditions under which the nanomaterials did not interfere with the fluorescent dyes for nitric oxide (DAF2) and superoxide (DHE), as these dyes are frequently used for in vivo studies.

TABLE 3

Antioxidant strength of carbon nanomaterials determined with a chemically based ORAC assay. [a]The above studies are described in more detail in Lucente-Schultz et al. (*J. Am. Chem. Soc.* 2009, 131, 3934-3941).

| Nanomaterial | Trolox Equivalents (TE) | Trolox Mass Equivalents (TME) |
| --- | --- | --- |
| p-SWNT | 14046 | 5.02 |
| PEG-HCC | 221 | 0.77 |
| Ionic BHT/PEG-HCC | 1240 | 4.31 |
| Covalent BHT/PEG-HCC | 532 | 1.85 |

[a]TE and TME values for HCC and SWNT samples were adjusted to account for the contribution of the corresponding solubilizing groups PEG and Pluronic respectively, by subtracting the TE and TME values found for each solubilizing group. Error range is 15%.

Figure 19:
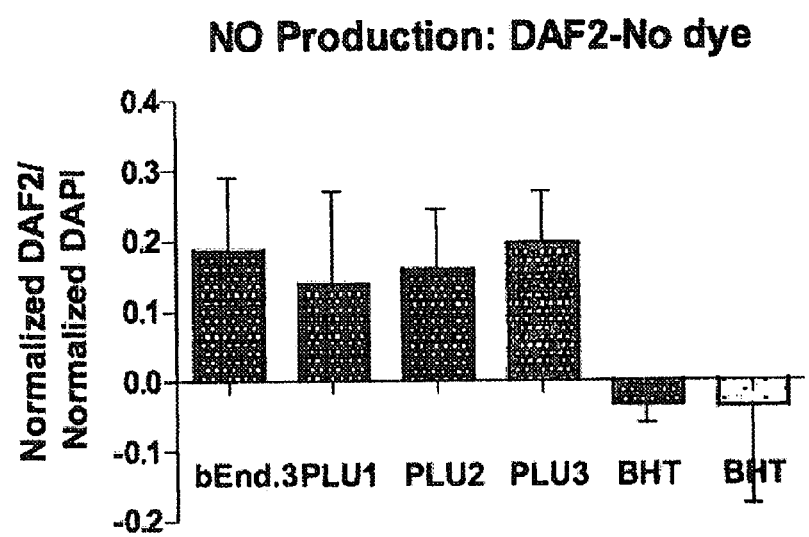
FIG. 19 shows the net production of Nitric Oxide as determined by fluorescence microscopy of cells treated with DAF-2 dye with background fluorescence subtracted in cultured endothelial cells (bEnd.3 cells). The results indicate only minimal effect of the pluronic single-walled nanotubes (SWNTs), but complete abolition by the butylated hydroxytoluene (BHT) modification.

Extensive in vitro testing with biologically relevant radicals indicated to Applicants that the PEG-HCCs and p-SWNTs were optimal in either their total anti-oxidative absorbance or specific superoxide scavenging activity. Applicants further confirmed the optimal antioxidant activities of PEG-HCCs and p-SWNTs with the finding that the ionic BHT/PEG-HCCs scavenged nitric oxide. See FIG. 19. However, the other antioxidants tested did not have such activities.

As set forth previously, Applicants have established that PEG-HCCs are capable of binding proteins and sequestering hydrophobic drugs for targeted in-vivo delivery. Accordingly, Applicants next aimed to determine whether antioxidants could also be utilized in the same manner.

Example 13.1

PEG-HCCs and ps/PEG-HCCs Reduce Oxidative Stress

As mentioned previously, PEG-HCCs have shown antioxidant activity in cell-free assays. Initially, Applicants explored protocols based on imaging the cells on a glass slide. While Applicants obtained promising results, the analysis was tedious and yielded relatively small differences. Thus, Applicants elected to pursue cellular antioxidant studies using cell flow cytometry.

P-selectin was chosen as the receptor to target for the antioxidant studies because it is overexpressed on injured endothelial cells after brain injury. It was also hypothesized that this strategy would have the additional advantage of treating cells with an agent that may address two targets: (1) oxidative stress; and (2) deleterious effects of adhesion molecule expression on endothelial cells.

Figure 20:
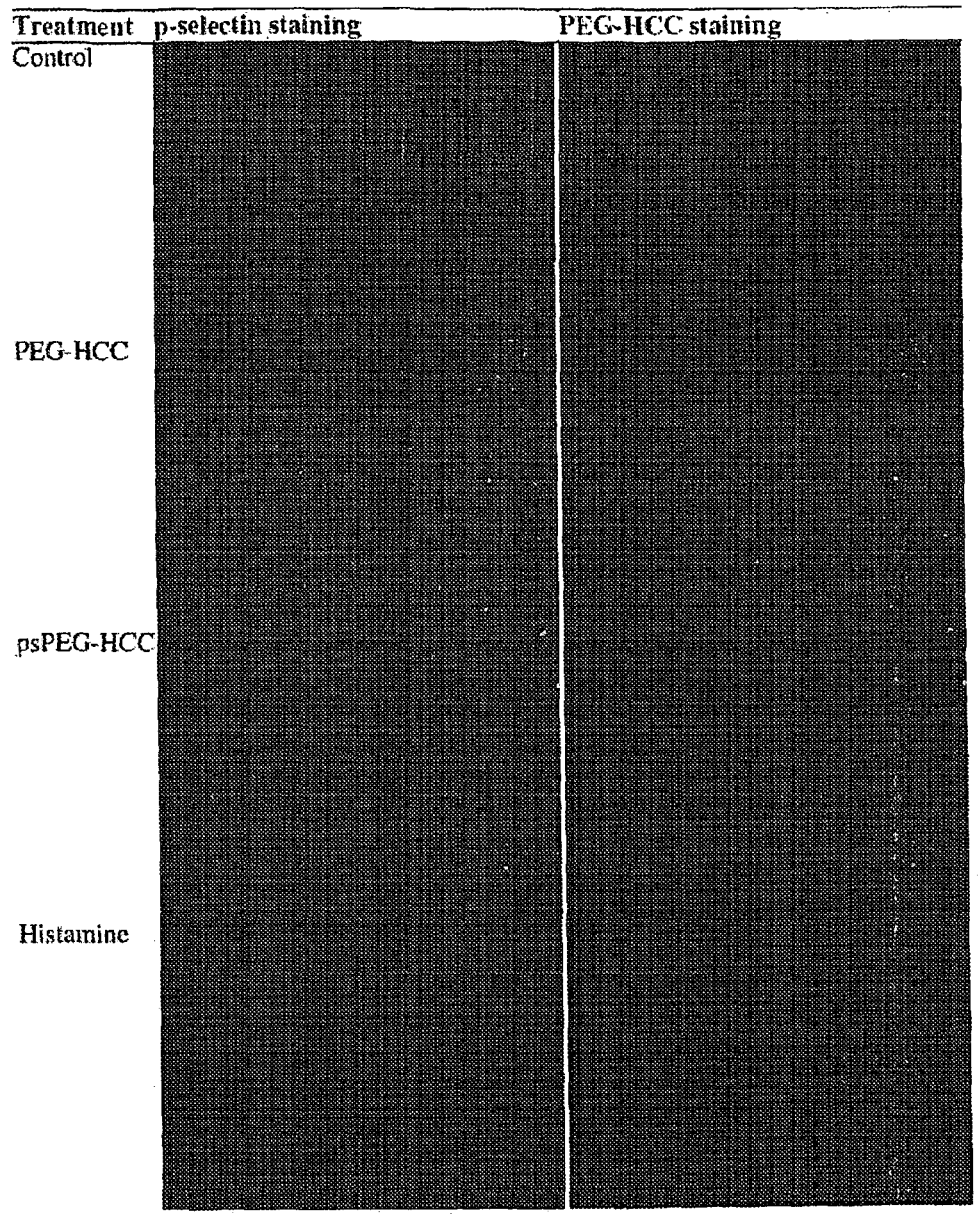
FIG. 20 shows results obtained from b.End3 cells that were stained for the presence of p-selectin (ps) and PEG-HCCs after various treatments.
Figure 20:
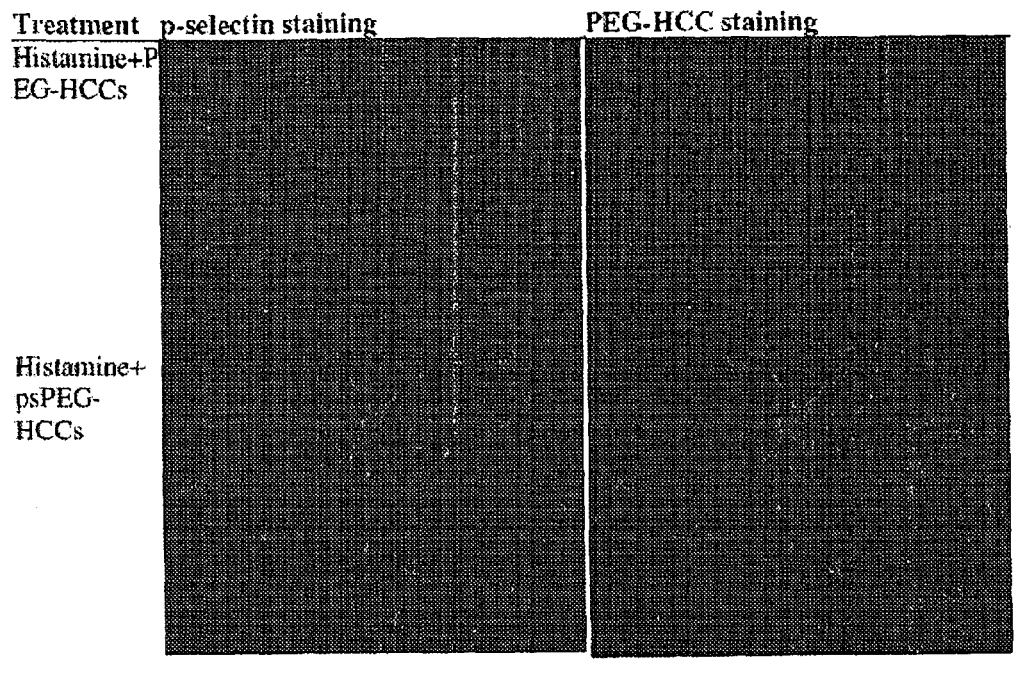

The expression of the p-selectin receptor can be induced in vitro by oxidatively stressing the cells via histamine treatment. Thus, in the experiments shown in FIG. 20, Applicants treated cells with or without histamine at time zero to induce p-selectin expression. After 15 minutes, Applicants treated the cells with PEG-HCCs or PEG-HCCs previously mixed with an anti-p-selectin antibody (psPEG-HCCs). Some cells also remained untreated for control purposes. The cells were then incubated for 15 minutes.

After washing and fixing, the cells were stained by a secondary antibody to the p-selectin antibody (red) to detect the binding of the anti-p-selectin antibody to p-selectin receptors. The cells were also stained with anti-PEG antibody (green) to detect the presence of PEG-HCCs. In addition, the cells' nuclei were stained with DAPI (blue).

In the cells that were not stimulated by histamine, Applicants primarily observed background binding along with some additional binding apparent with the p-selectin targeted PEG-HCCs. See FIG. 20A. However, Applicants observed a dramatic increase in binding with the targeted p-selectin antibody bound PEG-HCC's after p-selectin was stimulated by histamine. See FIG. 20B.

The above-mentioned experiment demonstrated the enhanced binding of the targeted HCCs to endothelial cells in a model that induces expression of a protein, p-selectin, known to be expressed in-vivo following brain injury. The next step was to establish whether addition of p-selectin antibody to the PEG-HCCs diminished their antioxidant ability.

Figure 21:
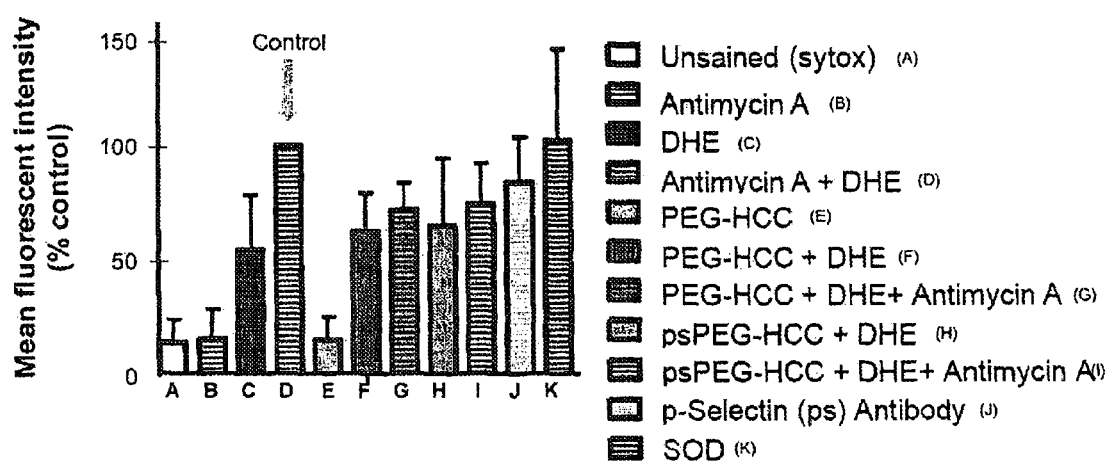
FIG. 21 shows that PEG-HCCs and ps/PEG-HCCs effectively reduce intracellular oxidative stress. Mean fluorescence intensity (indicative of oxidative stress) was measured using as control viable cells of 4 separated experiments treated with Antimycin A (AntA) and stained with dihydroethidine (DHE) ("AntA+DHE"). Results are given as % control (unstained cells) to account for minor differences in DHE concentrations and laser fluctuations.

Accordingly, the next series of experiments employed flow cytometry to assess antioxidant effectiveness of PEG-HCCs and targeted PEG-HCCs in cultured brain endothelial cells (b.End3 cells). For these experiments, bEnd.3 cells were cultured to 50-80% confluence in 6 well plates in 2 mL of culture media. The cells were treated with 10 μL of 2 mM Antimycin A (AntA, shown to induce intracellular superoxide radical production). Five minutes later, 1×PBS, PEG-HCC, psPEG-HCC or super oxide dismutase (SOD) was added. The cells were then incubated at 37° C. for 5 minutes. At that time, either 2 μL of 10 mM DHE or a 50% DMSO solution in 1×PBS (control) was added to the wells. The cells were then incubated for another 30 minutes. Next, the cells were placed on ice, trypsinized, and washed twice. The cells were then, counted and stained with SytoxRed (viability stain). 10,000 cells were analyzed per treatment group using the TXRED channel (DHE) and SytoxRed to assess cell viability. The obtained results are summarized in FIG. 21.

The results indicate that both the PEG-HCCs and the targeted psPEG-HCCs reduced the level of oxidative stress in Antimycin A treated cells to nearly baseline levels. There may be some intermediate efficacy of a p-selectin antibody although in this assay it did not reach Statistical significance. With such efficacy for the PEG-HCCs, Applicants could not differentiate between the activity of the PEG-HCCs and psPEG-HCCs. Nonetheless, it was reassuring that the targeted PEG-HCCs retained considerable antioxidant potential.

Applicants also note that in this oxidative stress model, treatment after Antimycin A with the antioxidants SOD, Trolox or PBN were not effective. However, HCC post-treatment was effective. In other subsequent experiments, Applicants found that treatment with much higher doses of SOD and PBN showed effectiveness. These observations reflect a difference in cellular permeation of the different materials.

Example 13.2

PEG-HCCs and pl/SWNTs Reduce Oxidative Stress

Figure 22:
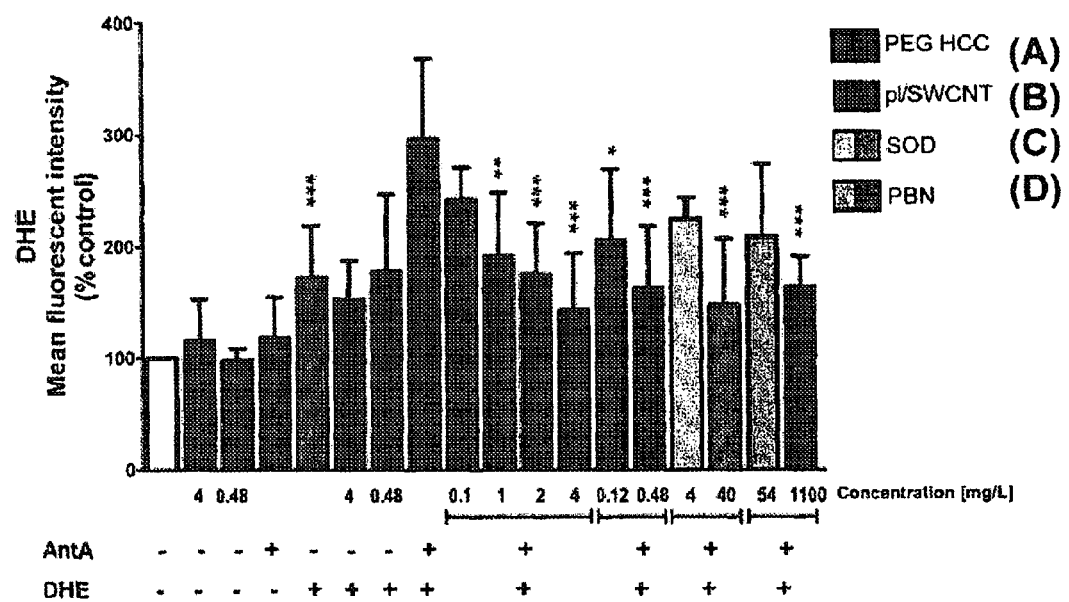
FIG. 22 illustrates a dose response curve showing that PEG-HCCs and pl/SWNTs reduce intracellular oxidative stress.

In order to better understand the activity of the PEG-HCCs and design future experiments to differentiate between the PEG-HCCs and psPEG-HCCs, a dose-response curve for the PEG-HCCs was performed. See FIG. 22. Briefly, bEnd.3 cells were grown in 6-well culture plates for 72 h. Culture media was reduced to 1 ml. Cells were treated with 1×PBS (5 µl/well) or 2 mM antimycin A (AntA; 5 µl/well; Sigma-Aldrich, St. Louis, Mo.), which induces intracellular reactive oxygen species (ROS). The cells were then incubated for 10 min at 37° C. and 5% $CO_2$. Antioxidant treatments were then given as follows: superoxide dismutase-polyethylene glycol (SOD; 40 U/well, 2 U/ul in PBS, Sigma-Aldrich), phenyl butyl nitrone (PBN; 20 µl/well; 300 mM; Acros Organics, Geel, Belgium), PEG-HCCs (1, 10, 20, 40 µl/well; 100 mg/l), and pl/SWCNT (10, 40 µl/well; 12 mg/l). Dihyroethidium (DHE; 1 µl/well; 5 mM; Fluka Chemie GmbH, Buchs, Switzerland) was added 5 min later and the cells were incubated at 37° C. and 5% $CO_2$ for 25 min. DHE reacts with ROS to form 2-hydroxyethidium, which possesses red fluorescence; thus, the increase in red fluorescence is proportional to the ROS in the sample. Cells were washed twice with 1×PBS, removed from the wells with 0.5 ml trypsin, suspended in 2 ml PBS with 2% fetal calf serum (FCS) in fluorescent-activated cell sorting (FACS) tubes, and washed twice. SytoxRED (1 µl; Invitrogen, Carlsbad, Calif.) was added to each tube. 15 min later, cells were run on a flow cytometer (BD FACSCanto II, San Jose, Calif.). For each sample, 10,000 cells were analyzed, and the mean fluorescent intensity (MF) was measured with assistance from the cytometry and cell sorting core (blue 488 nm laser for DHE detection and red 637 nm laser for SytoxRED detection). This is a measure of the level of DHE oxidation, which is proportional to the level of superoxide. Magnetic film imaging (MFI) for each experiment repetition was normalized to control cells from that individual experiment to avoid error due to daily fluctuations in the lasers.

Two additional control experiments were performed to test whether prolonged pretreatment exposure to known antioxidants was able to reduce superoxide levels from AntA exposure. In these cases, an identical procedure to that described above was followed, except that after the cells had grown in the 6-well plates for 58 h, they were treated with either 40 U/well PEG-SOD or 20 µl/well 300 mM PBN. 14 h later, at the 72 h time point, the cells were treated with 1×PBS (5 µl/well) or 2 mM AntA (5 µl/well). The cells were then incubated for 10 min at 37° C. and 5% $CO_2$. The cells were then treated again with either 40 U/well PEG-SOD or 20 µl/well 300 mM PBN. DHE staining and analysis was identical to that described above.

The results indicate that both the PEG-HCCs and the pl/SWNTs were able to quench the AntA-induced ROS in a dose-dependent manner. The pl/SWNTs were more potent, as a dose of just 0.48 mg/L of the pl/SWNTs lowered the amount of ROS to the background level, while a dose of 2-4 mg/L was required for the PEG-HCCs to achieve the same effect. Interestingly, when PEG-SOD or PBN was administered at a similar weight equivalent to the PEG-HCCs, no effect was observed. Without being bound by theory, this could be the result of more rapid internalization of the nanomaterials compared to the PEG-SOD and PBN.

Without further elaboration, it is believed that one skilled in the art can using the description herein, utilize the present invention to its fullest extent. The embodiments described herein are to be construed as illustrative and not as constraining the remainder of the disclosure in any way whatsoever. While some embodiments may involve particular mammals, the present invention encompasses other mammals, including experimental animals, companion animals, farm animals, primates and humans. While the preferred embodiments have been shown and described, many variations and modifications thereof can be made by one skilled in the art without departing from the spirit and teachings of the invention. Accordingly, the scope of protection is not limited by the description set out above; but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A therapeutic composition comprising:
  a. a nanovector,
    wherein said nanovector comprises an oxidized and ultra-short single-walled carbon nanotube (US-SWNT),
    wherein said US-SWNT has open ends,
    wherein said US-SWNT has lengths ranging from 20 nm to 80 nm,
    wherein said nanovector is polyethylene-glycol-functionalized, and
    wherein said nanovector is soluble in water;
  b. an active agent non-covalently associated with said nanovector,
    wherein said active agent comprises an anti-cancer drug; and
  c. a targeting agent non-covalently associated with said nanovector,
    wherein said targeting agent comprises an antibody.

2. The therapeutic composition of claim 1, wherein said active agent is selected from the group consisting of small molecules, proteins, DNA, antisense oligonucleotides, miRNA, siRNA, and aptamers.

3. The therapeutic composition of claim 1, wherein said active agent is Paclitaxel.

4. The therapeutic composition of claim 1, wherein said targeting agent comprises a monoclonal antibody.

5. The therapeutic composition of claim 1, wherein said targeting agent is an anti-epidermal growth factor receptor antibody.

6. A method of treating a condition in a subject, said method comprising administering a therapeutic composition to said subject, wherein said therapeutic composition comprises:
  a. a nanovector,
    wherein said nanovector comprises an oxidized and ultra-short single-walled carbon nanotube (US-SWNT),
    wherein said US-SWNT has open ends,
    wherein said US-SWNT has lengths ranging from 20 nm to 80 nm,
    wherein said nanovector is polyethylene-glycol-functionalized, and
    wherein said nanovector is soluble in water;
  b. an active agent non-covalently associated with said nanovector,
    wherein said active agent comprises an anti-cancer drug; and
  c. a targeting agent non-covalently associated with said nanovector,
    wherein said targeting agent comprises an antibody.

7. The method of claim 6, wherein said active agent comprises Paclitaxel, and said targeting agent comprises Cetuximab.

8. The method of claim 6, wherein said subject is a human being.

9. The method of claim 6, wherein said administering said therapeutic agent comprises intravenous administration.

10. The method of claim 6, further comprising administering radiation to said subject before, during or after said administering of said therapeutic composition.

11. A method of making a therapeutic composition, said method comprising:
   a. non-covalently associating a nanovector with an active agent
      wherein said active agent comprises an anti-cancer drug, and
      wherein said nanovector comprises an oxidized and ultra-short single-walled carbon nanotube (US-SWNT),
      wherein said US-SWNT has open ends,
      wherein said US-SWNT has lengths ranging from 20 nm to 80 nm,
      wherein said nanovector is polyethylene-glycol-functionalized, and
      wherein said nanovector is soluble in water; and
   b. non-covalently associating a targeting agent with said nanovector, wherein said targeting agent comprises an antibody.

12. The method of claim 11, wherein said associating of said nanovector with said active agent occurs by sequestration.

13. The method of claim 11, wherein said associating of said nanovector with said targeting agent occurs by sequestration.

* * * * *